United States Patent
Askem et al.

(10) Patent No.: US 12,370,300 B2
(45) Date of Patent: Jul. 29, 2025

(54) SYSTEMS AND METHODS FOR MONITORING ESSENTIAL PERFORMANCE OF WOUND THERAPY

(71) Applicant: T.J.Smith and Nephew, Limited, Hull (GB)

(72) Inventors: Ben Alan Askem, Leeds (GB); Iain Michael Blackburn, York (GB); David Michael Elder, Hull (GB); Edward Yerbury Hartwell, Hull (GB); Allan Kenneth Frazer Grugeon Hunt, Beverley (GB); Felix Clarence Quintanar, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 685 days.

(21) Appl. No.: 17/633,926

(22) PCT Filed: Aug. 12, 2020

(86) PCT No.: PCT/EP2020/072663
§ 371 (c)(1),
(2) Date: Feb. 8, 2022

(87) PCT Pub. No.: WO2021/028494
PCT Pub. Date: Feb. 18, 2021

(65) Prior Publication Data
US 2022/0288298 A1    Sep. 15, 2022

(30) Foreign Application Priority Data
Aug. 15, 2019    (GB) ...................................... 1911693

(51) Int. Cl.
*A61M 1/00*    (2006.01)

(52) U.S. Cl.
CPC ................ *A61M 1/73* (2021.05); *A61M 1/74* (2021.05); *A61M 1/915* (2021.05); *A61M 1/966* (2021.05);
(Continued)

(58) Field of Classification Search
CPC ........ A61M 1/966; A61M 1/962; A61M 1/96; A61M 1/95; A61M 1/90
See application file for complete search history.

(56) References Cited

U.S. PATENT DOCUMENTS

| 695,270 A | 3/1902 | Beringer |
| 3,194,239 A | 7/1965 | Sullivan et al. |

(Continued)

FOREIGN PATENT DOCUMENTS

| CN | 102961815 A | 3/2013 |
| CN | 104721892 A | 6/2015 |

(Continued)

OTHER PUBLICATIONS

Bon, M., "A Basic Introduction to BLE Security," retrieved from https://www.digikey.com/eewiki/display/Wireless/A+Basic+Introduction+to+BLE+Security, Oct. 25, 2016, 5 pages.
(Continued)

*Primary Examiner* — Guy K Townsend
*Assistant Examiner* — Peter Daniel Smith
(74) *Attorney, Agent, or Firm* — Knobbe, Martens, Olson & Bear, LLP

(57) ABSTRACT

A negative pressure wound therapy system can include a reduced pressure wound therapy device and a wound therapy monitoring device configured to emit an indication when it detects that at least one parameter associated with the provision of negative pressure wound therapy is outside an operational range. The wound therapy monitoring device can operate in a low power mode in which the at least one
(Continued)

parameter is periodically monitored. The reduced pressure wound therapy device can be configured to detect the indication and selectively generate an alarm. In some cases, the wound therapy monitoring device can be disposed in a wound or in a fluidic connector connecting the reduced pressure wound therapy device to the wound.

20 Claims, 10 Drawing Sheets

(52) U.S. Cl.
CPC .............. *A61M 1/912* (2021.05); *A61M 1/962* (2021.05); *A61M 1/964* (2021.05); *A61M 1/984* (2021.05); *A61M 2205/07* (2013.01); *A61M 2205/15* (2013.01); *A61M 2205/18* (2013.01); *A61M 2205/3344* (2013.01)

(56) References Cited

U.S. PATENT DOCUMENTS

| | | |
|---|---|---|
| 4,832,299 A | 5/1989 | Gorton et al. |
| 5,219,428 A | 6/1993 | Stern |
| 5,473,536 A | 12/1995 | Wimmer |
| 5,960,403 A | 9/1999 | Brown |
| 6,055,506 A | 4/2000 | Frasca et al. |
| 6,336,900 B1 | 1/2002 | Alleckson et al. |
| 6,353,445 B1 | 3/2002 | Babula et al. |
| 6,375,614 B1 | 4/2002 | Braun et al. |
| 6,385,622 B2 | 5/2002 | Bouve et al. |
| 6,406,426 B1 | 6/2002 | Reuss et al. |
| 6,434,572 B2 | 8/2002 | Derzay et al. |
| 6,460,041 B2 | 10/2002 | Lloyd |
| 6,574,518 B1 | 6/2003 | Lounsberry et al. |
| 6,640,145 B2 | 10/2003 | Hoffberg et al. |
| 6,640,246 B1 | 10/2003 | Gary et al. |
| 6,675,131 B2 | 1/2004 | Hahn |
| 6,681,003 B2 | 1/2004 | Linder et al. |
| 6,723,046 B2 | 4/2004 | Lichtenstein et al. |
| 6,730,024 B2 | 5/2004 | Freyre et al. |
| 6,747,556 B2 | 6/2004 | Medema et al. |
| 6,779,024 B2 | 8/2004 | DeLaHuerga |
| 6,782,285 B2 | 8/2004 | Birkenbach et al. |
| 6,856,825 B2 | 2/2005 | Hahn |
| 6,868,528 B2 | 3/2005 | Roberts |
| 6,871,211 B2 | 3/2005 | Labounty et al. |
| 6,909,974 B2 | 6/2005 | Yung et al. |
| 6,912,481 B2 | 6/2005 | Breunissen et al. |
| 6,961,731 B2 | 11/2005 | Holbrook |
| 7,004,915 B2 | 2/2006 | Boynton et al. |
| 7,022,113 B2 | 4/2006 | Lockwood et al. |
| 7,051,012 B2 | 5/2006 | Cole et al. |
| 7,062,251 B2 | 6/2006 | Birkett et al. |
| 7,066,883 B2 | 6/2006 | Schmidt et al. |
| 7,103,578 B2 | 9/2006 | Beck et al. |
| 7,108,683 B2 | 9/2006 | Zamierowski |
| 7,120,488 B2 | 10/2006 | Nova et al. |
| 7,133,869 B2 | 11/2006 | Bryan et al. |
| 7,167,858 B2 | 1/2007 | Naeymi-Rad et al. |
| 7,212,829 B1 | 5/2007 | Lau et al. |
| 7,264,591 B2 | 9/2007 | Brown |
| 7,300,418 B2 | 11/2007 | Zaleski |
| 7,304,573 B2 | 12/2007 | Postma |
| 7,311,665 B2 | 12/2007 | Hawthorne et al. |
| 7,333,002 B2 | 2/2008 | Bixler et al. |
| 7,353,179 B2 | 4/2008 | Ott et al. |
| 7,384,267 B1 | 6/2008 | Franks et al. |
| 7,430,598 B2 | 9/2008 | Raden et al. |
| 7,430,608 B2 | 9/2008 | Noonan et al. |
| 7,438,705 B2 | 10/2008 | Karpowicz et al. |
| 7,451,002 B2 | 11/2008 | Choubey |
| 7,457,804 B2 | 11/2008 | Uber et al. |
| 7,460,872 B2 | 12/2008 | Millard et al. |
| 7,534,240 B1 | 5/2009 | Johnson |
| 7,598,855 B2 | 10/2009 | Scalisi et al. |
| 7,608,066 B2 | 10/2009 | Vogel |
| 7,627,334 B2 | 12/2009 | Cohen et al. |
| 7,649,449 B2 | 1/2010 | Fenske et al. |
| 7,671,733 B2 | 3/2010 | McNeal et al. |
| 7,684,999 B2 | 3/2010 | Brown |
| 7,698,156 B2 | 4/2010 | Martucci et al. |
| 7,734,764 B2 | 6/2010 | Weiner et al. |
| 7,749,164 B2 | 7/2010 | Davis |
| 7,758,555 B2 | 7/2010 | Kelch et al. |
| 7,779,153 B2 | 8/2010 | Van Den Heuvel et al. |
| 7,789,828 B2 | 9/2010 | Clapp |
| 7,794,438 B2 | 9/2010 | Henley et al. |
| 7,827,148 B2 | 11/2010 | Mori et al. |
| 7,865,375 B2 | 1/2011 | Lancaster et al. |
| 7,889,069 B2 | 2/2011 | Fifolt et al. |
| 7,890,887 B1 | 2/2011 | Linardos et al. |
| 7,912,823 B2 | 3/2011 | Ferrari et al. |
| 7,925,603 B1 | 4/2011 | Laidig et al. |
| 7,933,817 B2 | 4/2011 | Radl et al. |
| 7,976,519 B2 | 7/2011 | Bubb et al. |
| 7,981,098 B2 | 7/2011 | Boehringer et al. |
| 7,988,850 B2 | 8/2011 | Roncadi et al. |
| 8,015,443 B2 | 9/2011 | Adachi |
| 8,015,972 B2 | 9/2011 | Pirzada |
| 8,019,618 B2 | 9/2011 | Brown |
| 8,036,925 B2 | 10/2011 | Choubey |
| 8,054,950 B1 | 11/2011 | Hung et al. |
| 8,069,057 B2 | 11/2011 | Choubey et al. |
| 8,094,009 B2 | 1/2012 | Allen et al. |
| 8,126,735 B2 | 2/2012 | Dicks et al. |
| 8,130,095 B2 | 3/2012 | Allen et al. |
| 8,131,472 B2 | 3/2012 | Chow et al. |
| 8,180,750 B2 | 5/2012 | Wilmering et al. |
| 8,190,445 B2 | 5/2012 | Kuth et al. |
| 8,190,448 B2 | 5/2012 | Bajars et al. |
| 8,228,188 B2 | 7/2012 | Key et al. |
| 8,246,606 B2 | 8/2012 | Stevenson et al. |
| 8,249,894 B2 | 8/2012 | Brown |
| 8,255,241 B2 | 8/2012 | Cafer |
| 8,260,630 B2 | 9/2012 | Brown |
| 8,280,682 B2 | 10/2012 | Vock et al. |
| 8,284,046 B2 | 10/2012 | Allen et al. |
| 8,290,792 B2 | 10/2012 | Sekura |
| 8,291,337 B2 | 10/2012 | Gannin et al. |
| 8,332,233 B2 | 12/2012 | Ott et al. |
| 8,332,236 B2 | 12/2012 | Yurko et al. |
| 8,334,768 B2 | 12/2012 | Eaton et al. |
| 8,360,975 B1 | 1/2013 | Schwieterman et al. |
| 8,361,056 B2 | 1/2013 | Wood et al. |
| 8,400,295 B1 | 3/2013 | Khaira |
| 8,422,377 B2 | 4/2013 | Weiner et al. |
| 8,424,517 B2 | 4/2013 | Sutherland et al. |
| 8,436,871 B2 | 5/2013 | Alberte |
| 8,439,882 B2 | 5/2013 | Kelch |
| 8,457,740 B2 | 6/2013 | Osche |
| 8,480,641 B2 | 7/2013 | Jacobs |
| 8,515,776 B2 | 8/2013 | Schoenberg |
| 8,532,764 B2 | 9/2013 | Duke |
| 8,540,688 B2 | 9/2013 | Eckstein et al. |
| 8,545,483 B2 | 10/2013 | Schwabe et al. |
| 8,554,195 B2 | 10/2013 | Rao |
| 8,554,902 B2 | 10/2013 | Ebert et al. |
| 8,558,964 B2 | 10/2013 | Bedingfield |
| 8,560,082 B2 | 10/2013 | Wei |
| 8,577,694 B2 | 11/2013 | Kanaan |
| 8,595,553 B2 | 11/2013 | Goertler et al. |
| 8,600,777 B2 | 12/2013 | Schoenberg et al. |
| 8,626,342 B2 | 1/2014 | Williams et al. |
| 8,626,526 B2 | 1/2014 | Lemke et al. |
| 8,630,660 B2 | 1/2014 | Ray et al. |
| 8,632,485 B2 | 1/2014 | Schlaeper et al. |
| 8,641,693 B2 | 2/2014 | Locke et al. |
| 8,659,420 B2 | 2/2014 | Salvat et al. |
| 8,676,597 B2 | 3/2014 | Buehler et al. |
| 8,689,008 B2 | 4/2014 | Rangadass et al. |
| 8,694,600 B2 | 4/2014 | Gaines et al. |
| 8,706,537 B1 | 4/2014 | Young et al. |
| 8,725,528 B2 | 5/2014 | Locke et al. |

(56) References Cited

U.S. PATENT DOCUMENTS

| | | |
|---|---|---|
| 8,756,078 B2 | 6/2014 | Collins et al. |
| 8,757,485 B2 | 6/2014 | Drees et al. |
| 8,758,315 B2 | 6/2014 | Chen et al. |
| 8,768,441 B2 | 7/2014 | De Zwart et al. |
| 8,769,625 B2 | 7/2014 | Wang et al. |
| 8,781,847 B2 | 7/2014 | Simms et al. |
| 8,795,171 B2 | 8/2014 | Adamczyk |
| 8,795,244 B2 | 8/2014 | Randolph et al. |
| 8,838,136 B2 | 9/2014 | Carnes et al. |
| 8,862,393 B2 | 10/2014 | Zhou et al. |
| 8,868,794 B2 | 10/2014 | Masoud et al. |
| 8,874,035 B2 | 10/2014 | Sherman et al. |
| 8,887,100 B1 | 11/2014 | Cook et al. |
| 8,890,656 B2 | 11/2014 | Pendse |
| 8,897,198 B2 | 11/2014 | Gaines et al. |
| 8,902,278 B2 | 12/2014 | Pinter et al. |
| 8,905,959 B2 | 12/2014 | Basaglia |
| 8,909,595 B2 | 12/2014 | Gandy et al. |
| 8,912,897 B2 | 12/2014 | Carnes |
| 8,922,377 B2 | 12/2014 | Carnes |
| 8,945,073 B2 | 2/2015 | Croizat et al. |
| 8,947,237 B2 | 2/2015 | Margon et al. |
| 8,976,062 B2 | 3/2015 | Park et al. |
| 8,978,026 B2 | 3/2015 | Charlton et al. |
| 8,996,393 B2 | 3/2015 | Sobie |
| 9,047,648 B1 | 6/2015 | Lekutai et al. |
| 9,058,634 B2 | 6/2015 | Buan et al. |
| 9,081,885 B2 | 7/2015 | Bangera et al. |
| 9,087,141 B2 | 7/2015 | Huang et al. |
| 9,092,705 B2 | 7/2015 | Zhuang |
| 9,098,114 B2 | 8/2015 | Potter et al. |
| 9,105,006 B2 | 8/2015 | Williamson |
| 9,114,054 B2 | 8/2015 | Bennett |
| 9,117,012 B2 | 8/2015 | Basaglia |
| 9,135,398 B2 | 9/2015 | Kaib et al. |
| 9,141,270 B1 | 9/2015 | Stuart et al. |
| 9,159,148 B2 | 10/2015 | Boyer et al. |
| 9,215,516 B2 | 12/2015 | Carnes et al. |
| 9,215,581 B2 | 12/2015 | Julian et al. |
| 9,230,420 B2 | 1/2016 | Lee et al. |
| 9,268,827 B2 | 2/2016 | Fernandez |
| 9,286,443 B2 | 3/2016 | Ford et al. |
| 9,323,893 B2 | 4/2016 | Berry et al. |
| 9,332,363 B2 | 5/2016 | Jain et al. |
| 9,338,819 B2 | 5/2016 | Meng et al. |
| 9,427,159 B2 | 8/2016 | Chang |
| 9,436,645 B2 | 9/2016 | Al-Ali et al. |
| 9,436,800 B2 | 9/2016 | Forrester |
| 9,439,584 B1 | 9/2016 | De Vries et al. |
| 9,460,431 B2 | 10/2016 | Curry |
| 9,474,679 B2 | 10/2016 | Locke et al. |
| 9,539,373 B2 | 1/2017 | Jones et al. |
| 9,545,466 B2 | 1/2017 | Locke et al. |
| 9,558,331 B2 | 1/2017 | Orona et al. |
| 9,585,565 B2 | 3/2017 | Carnes |
| 9,589,247 B2 | 3/2017 | Bolene et al. |
| 9,602,952 B2 | 3/2017 | Kang et al. |
| 9,629,986 B2 | 4/2017 | Patel et al. |
| 9,658,066 B2 | 5/2017 | Yuen et al. |
| 9,662,438 B2 | 5/2017 | Kamen et al. |
| 9,687,618 B2 | 6/2017 | Steinhauer et al. |
| 9,693,691 B2 | 7/2017 | Johnson |
| 9,700,462 B2 | 7/2017 | DeBusk et al. |
| 9,716,757 B2 | 7/2017 | Fernandes |
| 9,740,825 B2 | 8/2017 | Sansale et al. |
| 9,741,084 B2 | 8/2017 | Holmes et al. |
| 9,787,842 B1 | 10/2017 | Brooksby et al. |
| 9,792,660 B2 | 10/2017 | Cannon et al. |
| 9,817,948 B2 | 11/2017 | Swank |
| 9,818,164 B2 | 11/2017 | Nolte et al. |
| 9,838,645 B2 | 12/2017 | Hyde et al. |
| 9,878,081 B2 | 1/2018 | Leiendecker et al. |
| 9,905,123 B2 | 2/2018 | Lawhorn |
| 9,928,478 B2 | 3/2018 | Ragusky et al. |
| 9,974,492 B1 | 5/2018 | Dicks et al. |
| 9,990,466 B2 | 6/2018 | DeBusk et al. |
| 9,996,681 B2 | 6/2018 | Suarez et al. |
| 10,049,346 B2 | 8/2018 | Jensen et al. |
| 10,061,894 B2 | 8/2018 | Sethumadhavan et al. |
| 10,086,117 B2 | 10/2018 | Locke et al. |
| 10,095,649 B2 | 10/2018 | Joshua et al. |
| 10,127,357 B2 | 11/2018 | Whiting et al. |
| 10,152,575 B2 | 12/2018 | Sexton et al. |
| 10,173,008 B2 | 1/2019 | Simpson et al. |
| 10,185,834 B2 | 1/2019 | Adam et al. |
| 10,207,031 B2 | 2/2019 | Toth |
| 10,328,188 B2 | 6/2019 | Deutsch et al. |
| 10,549,017 B2 | 2/2020 | Hsiao et al. |
| 10,806,835 B2 | 10/2020 | Kelch et al. |
| 10,940,243 B2 | 3/2021 | Hall et al. |
| 10,959,884 B2 | 3/2021 | Rapp |
| 11,141,521 B2 | 10/2021 | Beadle et al. |
| 11,344,664 B2 * | 5/2022 | Locke ............... A61B 5/4833 |
| 11,883,262 B2 | 1/2024 | Cole et al. |
| 2002/0087360 A1 | 7/2002 | Pettit |
| 2002/0128804 A1 | 9/2002 | Geva |
| 2002/0128869 A1 | 9/2002 | Kuth |
| 2002/0135336 A1 | 9/2002 | Zhou et al. |
| 2002/0177757 A1 | 11/2002 | Britton |
| 2002/0184055 A1 | 12/2002 | Naghavi et al. |
| 2002/0198504 A1 | 12/2002 | Risk, Jr. et al. |
| 2003/0009244 A1 | 1/2003 | Engleson et al. |
| 2003/0018736 A1 | 1/2003 | Christ et al. |
| 2003/0105649 A1 | 6/2003 | Sheiner et al. |
| 2003/0114786 A1 | 6/2003 | Hiller et al. |
| 2003/0119568 A1 | 6/2003 | Menard |
| 2003/0182158 A1 | 9/2003 | Son |
| 2003/0221687 A1 | 12/2003 | Kaigler |
| 2003/0229518 A1 | 12/2003 | Abraham-Fuchs et al. |
| 2004/0006492 A1 | 1/2004 | Watanabe |
| 2004/0054775 A1 | 3/2004 | Poliac et al. |
| 2004/0078223 A1 | 4/2004 | Sacco et al. |
| 2004/0143458 A1 | 7/2004 | Pulkkinen et al. |
| 2004/0167802 A1 | 8/2004 | Takada et al. |
| 2004/0167804 A1 | 8/2004 | Simpson et al. |
| 2004/0172301 A1 | 9/2004 | Mihai et al. |
| 2004/0181433 A1 | 9/2004 | Blair |
| 2004/0193449 A1 | 9/2004 | Wildman et al. |
| 2004/0204962 A1 | 10/2004 | Howser et al. |
| 2005/0033124 A1 | 2/2005 | Kelly et al. |
| 2005/0055225 A1 | 3/2005 | Mehl |
| 2005/0055242 A1 | 3/2005 | Bello et al. |
| 2005/0055244 A1 | 3/2005 | Mullan et al. |
| 2005/0060211 A1 | 3/2005 | Xiao et al. |
| 2005/0065817 A1 | 3/2005 | Mihai et al. |
| 2005/0097200 A1 | 5/2005 | Denning, Jr. et al. |
| 2005/0102167 A1 | 5/2005 | Kapoor |
| 2005/0108046 A1 | 5/2005 | Craft |
| 2005/0108057 A1 | 5/2005 | Cohen et al. |
| 2005/0114176 A1 | 5/2005 | Dominick et al. |
| 2005/0119914 A1 | 6/2005 | Batch |
| 2005/0222873 A1 | 10/2005 | Nephin et al. |
| 2005/0240111 A1 | 10/2005 | Chung |
| 2005/0283382 A1 | 12/2005 | Donoghue et al. |
| 2006/0004604 A1 | 1/2006 | White |
| 2006/0064323 A1 | 3/2006 | Alleckson et al. |
| 2006/0085393 A1 | 4/2006 | Modesitt |
| 2006/0089539 A1 | 4/2006 | Miodownik et al. |
| 2006/0095853 A1 | 5/2006 | Amyot et al. |
| 2006/0155584 A1 | 7/2006 | Aggarwal |
| 2006/0161460 A1 | 7/2006 | Smitherman et al. |
| 2006/0190130 A1 | 8/2006 | Fedor et al. |
| 2006/0195843 A1 | 8/2006 | Hall |
| 2006/0246922 A1 | 11/2006 | Gasbarro et al. |
| 2007/0136099 A1 | 6/2007 | Neligh et al. |
| 2007/0156456 A1 | 7/2007 | McGillin et al. |
| 2007/0197881 A1 | 8/2007 | Wolf et al. |
| 2007/0219826 A1 | 9/2007 | Brodsky et al. |
| 2007/0255116 A1 | 11/2007 | Mehta et al. |
| 2007/0271298 A1 | 11/2007 | Juang et al. |
| 2008/0009681 A1 | 1/2008 | Al Hussiny |
| 2008/0086357 A1 | 4/2008 | Choubey et al. |
| 2008/0091659 A1 | 4/2008 | McFaul |
| 2008/0119705 A1 | 5/2008 | Patel et al. |

(56) References Cited

U.S. PATENT DOCUMENTS

| | | |
|---|---|---|
| 2008/0126126 A1 | 5/2008 | Ballai |
| 2008/0140160 A1 | 6/2008 | Goetz et al. |
| 2008/0167534 A1 | 7/2008 | Young et al. |
| 2008/0177579 A1 | 7/2008 | Dehaan |
| 2008/0221396 A1 | 9/2008 | Garces et al. |
| 2008/0242945 A1 | 10/2008 | Gugliotti et al. |
| 2008/0312953 A1 | 12/2008 | Claus |
| 2009/0037220 A1 | 2/2009 | Chambers et al. |
| 2009/0048492 A1 | 2/2009 | Rantala et al. |
| 2009/0048865 A1 | 2/2009 | Breazeale, Jr. |
| 2009/0097623 A1 | 4/2009 | Bharadwaj |
| 2009/0099867 A1 | 4/2009 | Newman |
| 2009/0115663 A1 | 5/2009 | Brown et al. |
| 2009/0118591 A1 | 5/2009 | Kim et al. |
| 2009/0125331 A1 | 5/2009 | Pamsgaard et al. |
| 2009/0136909 A1 | 5/2009 | Asukai et al. |
| 2009/0144091 A1 | 6/2009 | Rago |
| 2009/0157429 A1 | 6/2009 | Lee et al. |
| 2009/0163774 A1 | 6/2009 | Thatha et al. |
| 2009/0171166 A1 | 7/2009 | Amundson et al. |
| 2009/0177495 A1 | 7/2009 | Abousy et al. |
| 2009/0187424 A1 | 7/2009 | Grabowski |
| 2009/0204434 A1 | 8/2009 | Breazeale, Jr. |
| 2009/0204435 A1 | 8/2009 | Gale |
| 2009/0205042 A1 | 8/2009 | Zhou et al. |
| 2009/0224889 A1 | 9/2009 | Aggarwal et al. |
| 2009/0270833 A1 | 10/2009 | DeBelser et al. |
| 2009/0281822 A1 | 11/2009 | Warner et al. |
| 2009/0281830 A1 | 11/2009 | McNames et al. |
| 2009/0281867 A1 | 11/2009 | Sievenpiper et al. |
| 2009/0326339 A1 | 12/2009 | Horvitz |
| 2009/0327102 A1 | 12/2009 | Maniar et al. |
| 2010/0001838 A1 | 1/2010 | Miodownik et al. |
| 2010/0017471 A1 | 1/2010 | Brown et al. |
| 2010/0022848 A1 | 1/2010 | Lee et al. |
| 2010/0022990 A1 | 1/2010 | Karpowicz et al. |
| 2010/0030302 A1 | 2/2010 | Blowers et al. |
| 2010/0036333 A1 | 2/2010 | Schenk, III et al. |
| 2010/0090004 A1 | 4/2010 | Sands et al. |
| 2010/0106528 A1 | 4/2010 | Brackett et al. |
| 2010/0113908 A1 | 5/2010 | Vargas et al. |
| 2010/0145161 A1 | 6/2010 | Niyato et al. |
| 2010/0222645 A1 | 9/2010 | Nadler et al. |
| 2010/0234708 A1 | 9/2010 | Buck et al. |
| 2010/0255876 A1 | 10/2010 | Jordan et al. |
| 2011/0004188 A1 | 1/2011 | Shekalim |
| 2011/0066110 A1 | 3/2011 | Fathallah et al. |
| 2011/0071844 A1 | 3/2011 | Cannon et al. |
| 2011/0073107 A1 | 3/2011 | Rodman et al. |
| 2011/0077605 A1 | 3/2011 | Karpowicz et al. |
| 2011/0106561 A1 | 5/2011 | Eaton, Jr. et al. |
| 2011/0137759 A1 | 6/2011 | Wellington et al. |
| 2011/0145018 A1 | 6/2011 | Fotsch et al. |
| 2011/0173028 A1 | 7/2011 | Bond |
| 2011/0184754 A1 | 7/2011 | Park et al. |
| 2011/0225008 A1 | 9/2011 | Elkouh et al. |
| 2011/0246219 A1 | 10/2011 | Smith et al. |
| 2011/0275353 A1 | 11/2011 | Liu |
| 2011/0288535 A1* | 11/2011 | Locke ............... A61M 1/966 137/15.01 |
| 2011/0288878 A1 | 11/2011 | Blair |
| 2012/0029312 A1 | 2/2012 | Beaudry et al. |
| 2012/0029313 A1 | 2/2012 | Burdett et al. |
| 2012/0032819 A1 | 2/2012 | Chae et al. |
| 2012/0035427 A1 | 2/2012 | Friedman et al. |
| 2012/0077605 A1 | 3/2012 | Nakagaito et al. |
| 2012/0081225 A1 | 4/2012 | Waugh et al. |
| 2012/0086543 A1* | 4/2012 | Kuo ............... A61B 5/0022 340/3.31 |
| 2012/0089369 A1 | 4/2012 | Abuzeni et al. |
| 2012/0109034 A1 | 5/2012 | Locke et al. |
| 2012/0123323 A1 | 5/2012 | Kagan et al. |
| 2012/0123796 A1 | 5/2012 | McFaul |
| 2012/0157889 A1 | 6/2012 | Tanis et al. |
| 2012/0181405 A1 | 7/2012 | Zlatic et al. |
| 2012/0182143 A1 | 7/2012 | Gaines et al. |
| 2012/0191475 A1 | 7/2012 | Pandey |
| 2012/0212455 A1 | 8/2012 | Kloeffel |
| 2012/0215455 A1 | 8/2012 | Patil et al. |
| 2012/0259651 A1 | 10/2012 | Mallon et al. |
| 2012/0271256 A1 | 10/2012 | Locke et al. |
| 2012/0290217 A1 | 11/2012 | Shoval et al. |
| 2012/0295566 A1 | 11/2012 | Collins et al. |
| 2012/0310205 A1 | 12/2012 | Lee et al. |
| 2013/0018355 A1 | 1/2013 | Brand et al. |
| 2013/0035615 A1 | 2/2013 | Hsieh |
| 2013/0045764 A1 | 2/2013 | Vik et al. |
| 2013/0073303 A1 | 3/2013 | Hsu |
| 2013/0076528 A1 | 3/2013 | Boettner et al. |
| 2013/0087609 A1 | 4/2013 | Nichol et al. |
| 2013/0090949 A1 | 4/2013 | Tibebu |
| 2013/0103419 A1 | 4/2013 | Beaudry |
| 2013/0124227 A1 | 5/2013 | Ellis |
| 2013/0132855 A1 | 5/2013 | Manicka et al. |
| 2013/0150686 A1 | 6/2013 | Fronterhouse et al. |
| 2013/0150698 A1 | 6/2013 | Hsu et al. |
| 2013/0151274 A1 | 6/2013 | Bage et al. |
| 2013/0157571 A1 | 6/2013 | Wondka et al. |
| 2013/0159456 A1 | 6/2013 | Daoud et al. |
| 2013/0160082 A1 | 6/2013 | Miller |
| 2013/0186405 A1 | 7/2013 | Krzyzanowski et al. |
| 2013/0190903 A1 | 7/2013 | Balakrishnan et al. |
| 2013/0191513 A1 | 7/2013 | Kamen et al. |
| 2013/0196703 A1 | 8/2013 | Masoud et al. |
| 2013/0204106 A1 | 8/2013 | Bennett |
| 2013/0211206 A1 | 8/2013 | Sands et al. |
| 2013/0211854 A1 | 8/2013 | Wagstaff |
| 2013/0212168 A1 | 8/2013 | Bonasera et al. |
| 2013/0214925 A1 | 8/2013 | Weiss |
| 2013/0218053 A1 | 8/2013 | Kaiser et al. |
| 2013/0226607 A1 | 8/2013 | Woody et al. |
| 2013/0227128 A1 | 8/2013 | Wagstaff |
| 2013/0231596 A1 | 9/2013 | Hornbach et al. |
| 2013/0245387 A1 | 9/2013 | Patel |
| 2013/0253952 A1 | 9/2013 | Burke et al. |
| 2013/0255681 A1 | 10/2013 | Batch et al. |
| 2013/0267919 A1 | 10/2013 | Caso et al. |
| 2013/0267920 A1* | 10/2013 | Nicolini ............... A61M 1/73 604/319 |
| 2013/0268283 A1 | 10/2013 | Vann et al. |
| 2013/0271556 A1 | 10/2013 | Ross et al. |
| 2013/0282395 A1 | 10/2013 | Rustgi et al. |
| 2013/0285837 A1 | 10/2013 | Uchida |
| 2013/0297350 A1 | 11/2013 | Gross et al. |
| 2013/0304489 A1 | 11/2013 | Miller |
| 2013/0310726 A1 | 11/2013 | Miller et al. |
| 2013/0317753 A1 | 11/2013 | Kamen et al. |
| 2013/0317837 A1 | 11/2013 | Ballantyne et al. |
| 2013/0325508 A1 | 12/2013 | Johnson et al. |
| 2013/0331748 A1 | 12/2013 | Wright et al. |
| 2013/0332197 A1 | 12/2013 | Hinkel |
| 2013/0335233 A1 | 12/2013 | Kamar et al. |
| 2013/0339049 A1 | 12/2013 | Blumberg, Jr. et al. |
| 2013/0345524 A1 | 12/2013 | Meyer et al. |
| 2014/0002234 A1 | 1/2014 | Alwan |
| 2014/0028464 A1 | 1/2014 | Garibaldi |
| 2014/0031884 A1 | 1/2014 | Elghazzawi |
| 2014/0032231 A1 | 1/2014 | Semen et al. |
| 2014/0058714 A1 | 2/2014 | Boyer |
| 2014/0087762 A1 | 3/2014 | Galvin et al. |
| 2014/0108033 A1 | 4/2014 | Akbay et al. |
| 2014/0108034 A1 | 4/2014 | Akbay et al. |
| 2014/0108035 A1 | 4/2014 | Akbay et al. |
| 2014/0129250 A1 | 5/2014 | Daniel et al. |
| 2014/0148138 A1 | 5/2014 | Chou |
| 2014/0171753 A1 | 6/2014 | Montejo et al. |
| 2014/0187888 A1 | 7/2014 | Hatziantoniou |
| 2014/0207090 A1 | 7/2014 | Jian |
| 2014/0221787 A1 | 8/2014 | Teller et al. |
| 2014/0221788 A1 | 8/2014 | Teller et al. |
| 2014/0222446 A1 | 8/2014 | Ash et al. |
| 2014/0235166 A1 | 8/2014 | Molettiere et al. |
| 2014/0235975 A1 | 8/2014 | Carnes |
| 2014/0244285 A1 | 8/2014 | Hinkle et al. |

(56) References Cited

U.S. PATENT DOCUMENTS

| | | |
|---|---|---|
| 2014/0244301 A1 | 8/2014 | Lee et al. |
| 2014/0244307 A1 | 8/2014 | Shutko et al. |
| 2014/0266713 A1 | 9/2014 | Sehgal et al. |
| 2014/0275876 A1 | 9/2014 | Hansen et al. |
| 2014/0278502 A1 | 9/2014 | Laskin |
| 2014/0280882 A1 | 9/2014 | Lacerte et al. |
| 2014/0297299 A1 | 10/2014 | Lester, IV |
| 2014/0316819 A1 | 10/2014 | Dunsirn et al. |
| 2014/0350966 A1 | 11/2014 | Khatana et al. |
| 2014/0366878 A1 | 12/2014 | Baron |
| 2014/0372147 A1 | 12/2014 | White |
| 2014/0372522 A1 | 12/2014 | Orona et al. |
| 2014/0375470 A1 | 12/2014 | Malveaux |
| 2014/0378895 A1 | 12/2014 | Barack |
| 2015/0011970 A1 | 1/2015 | Kamen et al. |
| 2015/0012290 A1 | 1/2015 | Inciardi et al. |
| 2015/0019237 A1 | 1/2015 | Doyle et al. |
| 2015/0019257 A1 | 1/2015 | Doyle et al. |
| 2015/0025486 A1 | 1/2015 | Hu et al. |
| 2015/0046137 A1 | 2/2015 | Zeilinger |
| 2015/0066531 A1 | 3/2015 | Jacobson et al. |
| 2015/0072613 A1 | 3/2015 | Swanson |
| 2015/0094830 A1 | 4/2015 | Lipoma et al. |
| 2015/0095059 A1 | 4/2015 | Yegge et al. |
| 2015/0100340 A1 | 4/2015 | Folsom et al. |
| 2015/0112707 A1 | 4/2015 | Manice et al. |
| 2015/0118662 A1 | 4/2015 | Ellison et al. |
| 2015/0119652 A1 | 4/2015 | Hyde et al. |
| 2015/0120318 A1 | 4/2015 | Toyama |
| 2015/0143300 A1 | 5/2015 | Zhang et al. |
| 2015/0164323 A1 | 6/2015 | Holtzclaw |
| 2015/0164376 A1 | 6/2015 | Huang |
| 2015/0186615 A1 | 7/2015 | Armor et al. |
| 2015/0189001 A1 | 7/2015 | Lee et al. |
| 2015/0223278 A1 | 8/2015 | Reaston et al. |
| 2015/0228043 A1 | 8/2015 | Ryan et al. |
| 2015/0234557 A1 | 8/2015 | Dorn |
| 2015/0234995 A1 | 8/2015 | Casady et al. |
| 2015/0242578 A1 | 8/2015 | Siemon |
| 2015/0242583 A1 | 8/2015 | Edson |
| 2015/0254403 A1 | 9/2015 | Laperna |
| 2015/0257643 A1 | 9/2015 | Watson et al. |
| 2015/0261920 A1 | 9/2015 | Blick |
| 2015/0269323 A1 | 9/2015 | Ginsburg |
| 2015/0286970 A1 | 10/2015 | Dickerson et al. |
| 2015/0304478 A1 | 10/2015 | Kim et al. |
| 2015/0310182 A1 | 10/2015 | Henze et al. |
| 2015/0324943 A1 | 11/2015 | Han et al. |
| 2015/0339445 A1 | 11/2015 | Gruby et al. |
| 2015/0363058 A1 | 12/2015 | Chung et al. |
| 2015/0370984 A1 | 12/2015 | Russell et al. |
| 2015/0370997 A1 | 12/2015 | Krongrad et al. |
| 2015/0379441 A1 | 12/2015 | Syed et al. |
| 2016/0004824 A1 | 1/2016 | Stanton et al. |
| 2016/0018963 A1 | 1/2016 | Robbins et al. |
| 2016/0042154 A1 | 2/2016 | Goldberg et al. |
| 2016/0044141 A1 | 2/2016 | Pfützenreuter et al. |
| 2016/0055310 A1 | 2/2016 | Bentley et al. |
| 2016/0058286 A1 | 3/2016 | Joshua et al. |
| 2016/0063210 A1 | 3/2016 | Bardi et al. |
| 2016/0066864 A1 | 3/2016 | Frieder et al. |
| 2016/0080365 A1 | 3/2016 | Baker et al. |
| 2016/0085415 A1 | 3/2016 | Humphrys et al. |
| 2016/0098524 A1 | 4/2016 | Himmelstein |
| 2016/0110507 A1 | 4/2016 | Abbo |
| 2016/0128571 A1 | 5/2016 | Adler |
| 2016/0129186 A1 | 5/2016 | Douglas et al. |
| 2016/0135752 A1 | 5/2016 | Beaumont |
| 2016/0142443 A1 | 5/2016 | Ting et al. |
| 2016/0151015 A1 | 6/2016 | Condurso et al. |
| 2016/0154936 A1 | 6/2016 | Kalathil |
| 2016/0154943 A1 | 6/2016 | Cho et al. |
| 2016/0171866 A1 | 6/2016 | Dupasquier et al. |
| 2016/0180031 A1 | 6/2016 | Slater |
| 2016/0184497 A1 | 6/2016 | Phillips et al. |
| 2016/0196399 A1 | 7/2016 | Bonhomme |
| 2016/0203275 A1 | 7/2016 | Benjamin et al. |
| 2016/0203283 A1 | 7/2016 | Baruah et al. |
| 2016/0209837 A1 | 7/2016 | Kim |
| 2016/0212577 A1 | 7/2016 | Dor et al. |
| 2016/0217433 A1 | 7/2016 | Walton et al. |
| 2016/0246943 A1 | 8/2016 | Lake et al. |
| 2016/0260035 A1 | 9/2016 | Crooks et al. |
| 2016/0261974 A1 | 9/2016 | Arrizza |
| 2016/0287189 A1 | 10/2016 | Modai et al. |
| 2016/0308969 A1 | 10/2016 | Aihara et al. |
| 2016/0321404 A1 | 11/2016 | Ginsburg |
| 2016/0321422 A1 | 11/2016 | Albright |
| 2017/0004271 A1 | 1/2017 | Ash et al. |
| 2017/0007494 A1 | 1/2017 | Rock et al. |
| 2017/0014028 A1 | 1/2017 | Clear, Jr. |
| 2017/0017765 A1 | 1/2017 | Yegge et al. |
| 2017/0032648 A1 | 2/2017 | McClain et al. |
| 2017/0046503 A1 | 2/2017 | Cho et al. |
| 2017/0053073 A1 | 2/2017 | Allen et al. |
| 2017/0055205 A1 | 2/2017 | Morris et al. |
| 2017/0065751 A1* | 3/2017 | Toth ............... A61M 1/74 |
| 2017/0068781 A1 | 3/2017 | Zasowski et al. |
| 2017/0074717 A1 | 3/2017 | Pilkington et al. |
| 2017/0078396 A1 | 3/2017 | Haas et al. |
| 2017/0094446 A1 | 3/2017 | Maggiore |
| 2017/0116373 A1 | 4/2017 | Ginsburg et al. |
| 2017/0140120 A1 | 5/2017 | Thrower |
| 2017/0150939 A1 | 6/2017 | Shah |
| 2017/0193181 A1 | 7/2017 | Carter et al. |
| 2017/0212995 A1 | 7/2017 | Ingmanson |
| 2017/0220755 A1 | 8/2017 | Fowler et al. |
| 2017/0239412 A1 | 8/2017 | Court |
| 2017/0257682 A1 | 9/2017 | Shtalryd |
| 2017/0270533 A1 | 9/2017 | Barton et al. |
| 2017/0273116 A1 | 9/2017 | Elghazzawi |
| 2017/0327371 A1 | 11/2017 | Bai et al. |
| 2017/0372010 A1 | 12/2017 | Doherty et al. |
| 2018/0000501 A1* | 1/2018 | Baym ............... A61B 34/32 |
| 2018/0004908 A1 | 1/2018 | Barrus et al. |
| 2018/0052454 A1 | 2/2018 | Magno et al. |
| 2018/0060529 A1 | 3/2018 | Crothall et al. |
| 2018/0121629 A1 | 5/2018 | Dyer et al. |
| 2018/0139572 A1 | 5/2018 | Hansen |
| 2018/0144817 A1 | 5/2018 | Lofgren et al. |
| 2018/0158545 A1 | 6/2018 | Blomquist |
| 2018/0160907 A1 | 6/2018 | Verma |
| 2018/0181714 A1 | 6/2018 | Pillarisetty et al. |
| 2018/0233016 A1 | 8/2018 | Daniel et al. |
| 2018/0233221 A1 | 8/2018 | Blomquist |
| 2018/0234499 A1 | 8/2018 | Borges et al. |
| 2018/0279880 A1 | 10/2018 | Bacchi |
| 2018/0286502 A1 | 10/2018 | Lane et al. |
| 2018/0308569 A1 | 10/2018 | Luellen |
| 2018/0308573 A1 | 10/2018 | Hochrein et al. |
| 2018/0315492 A1 | 11/2018 | Bishop et al. |
| 2018/0322944 A1 | 11/2018 | Valdizan |
| 2019/0046697 A1 | 2/2019 | Locke et al. |
| 2019/0374689 A1* | 12/2019 | Coulthard ............... A61M 1/75 |
| 2020/0306423 A1 | 10/2020 | Tharan et al. |
| 2021/0169401 A1 | 6/2021 | Drennan |

FOREIGN PATENT DOCUMENTS

| | | |
|---|---|---|
| CN | 106580558 A | 4/2017 |
| CN | 107714295 A | 2/2018 |
| DE | 102010036405 A1 | 1/2012 |
| EP | 0980227 A1 | 2/2000 |
| EP | 0566381 B1 | 7/2002 |
| EP | 1231965 A2 | 8/2002 |
| EP | 1291802 A2 | 3/2003 |
| EP | 1309960 A1 | 5/2003 |
| EP | 0814864 B1 | 12/2003 |
| EP | 1407624 A2 | 4/2004 |
| EP | 1011420 B1 | 12/2004 |
| EP | 1495713 A1 | 1/2005 |
| EP | 1524619 A2 | 4/2005 |
| EP | 1540557 A2 | 6/2005 |
| EP | 1579367 A2 | 9/2005 |

(56) References Cited

FOREIGN PATENT DOCUMENTS

| | | |
|---|---|---|
| EP | 1587017 A2 | 10/2005 |
| EP | 1788503 A2 | 5/2007 |
| EP | 1839244 A1 | 10/2007 |
| EP | 1839615 A1 | 10/2007 |
| EP | 1857950 A2 | 11/2007 |
| EP | 1870068 A1 | 12/2007 |
| EP | 1904964 A1 | 4/2008 |
| EP | 1934852 A1 | 6/2008 |
| EP | 1975828 A2 | 10/2008 |
| EP | 1993435 A2 | 11/2008 |
| EP | 2038786 A2 | 3/2009 |
| EP | 2040604 A2 | 4/2009 |
| EP | 2092470 A2 | 8/2009 |
| EP | 2146297 A1 | 1/2010 |
| EP | 2172859 A1 | 4/2010 |
| EP | 2214552 A1 | 8/2010 |
| EP | 2218478 A1 | 8/2010 |
| EP | 1404213 B1 | 3/2011 |
| EP | 1247229 B1 | 4/2011 |
| EP | 1406540 B1 | 6/2011 |
| EP | 1812094 B1 | 8/2011 |
| EP | 2384472 A1 | 11/2011 |
| EP | 2226002 B1 | 1/2012 |
| EP | 1610494 B1 | 3/2012 |
| EP | 1248660 B1 | 4/2012 |
| EP | 2023800 B1 | 4/2012 |
| EP | 2451513 A1 | 5/2012 |
| EP | 1248661 B1 | 8/2012 |
| EP | 2488977 A1 | 8/2012 |
| EP | 2562665 A2 | 2/2013 |
| EP | 2619723 A2 | 7/2013 |
| EP | 1881784 B1 | 10/2013 |
| EP | 2647395 A1 | 10/2013 |
| EP | 2664194 A2 | 11/2013 |
| EP | 2743850 A2 | 6/2014 |
| EP | 2745204 A1 | 6/2014 |
| EP | 1684146 B1 | 7/2014 |
| EP | 2841895 A1 | 3/2015 |
| EP | 2850771 A1 | 3/2015 |
| EP | 2876567 A1 | 5/2015 |
| EP | 2891999 A2 | 7/2015 |
| EP | 2894581 A1 | 7/2015 |
| EP | 2906101 A2 | 8/2015 |
| EP | 2945084 A1 | 11/2015 |
| EP | 2962266 A1 | 1/2016 |
| EP | 2968829 A1 | 1/2016 |
| EP | 2973089 A1 | 1/2016 |
| EP | 3000082 A1 | 3/2016 |
| EP | 3009946 A1 | 4/2016 |
| EP | 3010398 A1 | 4/2016 |
| EP | 3054389 A2 | 8/2016 |
| EP | 3070628 A1 | 9/2016 |
| EP | 3078010 A1 | 10/2016 |
| EP | 3096113 A1 | 11/2016 |
| EP | 2563437 B1 | 3/2017 |
| EP | 2773393 B1 | 3/2017 |
| EP | 3134854 A1 | 3/2017 |
| EP | 3027242 B1 | 4/2017 |
| EP | 2556650 B1 | 5/2017 |
| EP | 3209358 A1 | 8/2017 |
| EP | 3041571 B1 | 9/2017 |
| EP | 2856767 B1 | 11/2017 |
| EP | 3252635 A1 | 12/2017 |
| EP | 2320971 B1 | 5/2018 |
| EP | 2335173 B1 | 5/2018 |
| EP | 3100188 B1 | 6/2018 |
| EP | 3330973 A1 | 6/2018 |
| EP | 3352174 A1 | 7/2018 |
| EP | 2440112 B1 | 10/2018 |
| EP | 3400549 A1 | 11/2018 |
| EP | 2992500 B1 | 12/2018 |
| EP | 2597584 B1 | 1/2019 |
| EP | 3219340 B1 | 1/2019 |
| EP | 2890456 B1 | 2/2019 |
| EP | 3377130 B1 | 4/2019 |
| EP | 2881875 B1 | 5/2019 |
| EP | 2836269 B1 | 8/2019 |
| EP | 4045102 A1 | 8/2022 |
| GB | 2409951 A | 7/2005 |
| GB | 2436160 A | 9/2007 |
| GB | 2449400 A | 11/2008 |
| GB | 2456708 A | 7/2009 |
| GB | 2423178 B | 5/2010 |
| GB | 2475091 A | 5/2011 |
| GB | 2488904 A | 9/2012 |
| GB | 2446923 B | 5/2013 |
| GB | 2499986 A | 9/2013 |
| GB | 2491946 B | 8/2014 |
| GB | 2499873 B | 5/2016 |
| GB | 2533910 A | 7/2016 |
| GB | 2541286 A | 2/2017 |
| GB | 2550576 B | 6/2018 |
| WO | WO-9627163 A1 | 9/1996 |
| WO | WO-9744745 A1 | 11/1997 |
| WO | WO-9924927 A1 | 5/1999 |
| WO | WO-9963886 A1 | 12/1999 |
| WO | WO-0032088 A1 | 6/2000 |
| WO | WO-0060522 A2 | 10/2000 |
| WO | WO-0133457 A1 | 5/2001 |
| WO | WO-0181829 A1 | 11/2001 |
| WO | WO-0217075 A2 | 2/2002 |
| WO | WO-0233577 A1 | 4/2002 |
| WO | WO-02078594 A2 | 10/2002 |
| WO | WO-02101713 A1 | 12/2002 |
| WO | WO-03054668 A2 | 7/2003 |
| WO | WO-2004057514 A2 | 7/2004 |
| WO | WO-2004074457 A2 | 9/2004 |
| WO | WO-2005022349 A2 | 3/2005 |
| WO | WO-2005031632 A2 | 4/2005 |
| WO | WO-2005036447 A2 | 4/2005 |
| WO | WO-2005045461 A1 | 5/2005 |
| WO | WO-2005053793 A1 | 6/2005 |
| WO | WO-2005057466 A2 | 6/2005 |
| WO | WO-2005083619 A2 | 9/2005 |
| WO | WO-2005101282 A2 | 10/2005 |
| WO | WO-2005109297 A2 | 11/2005 |
| WO | WO-2005120097 A2 | 12/2005 |
| WO | WO-2006021154 A1 | 3/2006 |
| WO | WO-2006066583 A1 | 6/2006 |
| WO | WO-2006066585 A2 | 6/2006 |
| WO | WO-2006071711 A2 | 7/2006 |
| WO | WO-2006099120 A2 | 9/2006 |
| WO | WO-2006108304 A1 | 10/2006 |
| WO | WO-2006108858 A1 | 10/2006 |
| WO | WO-2006111109 A1 | 10/2006 |
| WO | WO-2007027490 A2 | 3/2007 |
| WO | WO-2007035646 A2 | 3/2007 |
| WO | WO-2007127879 A2 | 11/2007 |
| WO | WO-2007133478 A2 | 11/2007 |
| WO | WO-2007137869 A2 | 12/2007 |
| WO | WO-2008010012 A2 | 1/2008 |
| WO | WO-2008036344 A1 | 3/2008 |
| WO | WO-2008062382 A2 | 5/2008 |
| WO | WO-2008116295 A1 | 10/2008 |
| WO | WO-2008150633 A2 | 12/2008 |
| WO | WO-2009140669 A2 | 11/2009 |
| WO | WO-2010017484 A2 | 2/2010 |
| WO | WO-2010025166 A1 | 3/2010 |
| WO | WO-2010025467 A1 | 3/2010 |
| WO | WO-2010078558 A1 | 7/2010 |
| WO | WO-2010085033 A2 | 7/2010 |
| WO | WO-2010132617 A2 | 11/2010 |
| WO | WO-2010145780 A1 | 12/2010 |
| WO | WO-2011005633 A2 | 1/2011 |
| WO | WO-2011023384 A1 | 3/2011 |
| WO | WO-2011039676 A2 | 4/2011 |
| WO | WO-2011046860 A1 | 4/2011 |
| WO | WO-2011047334 A1 | 4/2011 |
| WO | WO-2011137230 A1 | 11/2011 |
| WO | WO-2012051278 A1 | 4/2012 |
| WO | WO-2012127281 A1 | 9/2012 |
| WO | WO-2013026999 A1 | 2/2013 |
| WO | WO-2013036853 A2 | 3/2013 |
| WO | WO-2013061887 A1 | 5/2013 |

(56) References Cited

FOREIGN PATENT DOCUMENTS

| | | |
|---|---|---|
| WO | WO-2013078095 A2 | 5/2013 |
| WO | WO-2013102855 A1 | 7/2013 |
| WO | WO-2013109517 A1 | 7/2013 |
| WO | WO-2013138182 A1 | 9/2013 |
| WO | WO-2013141870 A1 | 9/2013 |
| WO | WO-2013155193 A1 | 10/2013 |
| WO | WO-2013175076 A1 | 11/2013 |
| WO | WO-2014015215 A2 | 1/2014 |
| WO | WO-2014018786 A2 | 1/2014 |
| WO | WO-2014075494 A1 | 5/2014 |
| WO | WO-2014089086 A1 | 6/2014 |
| WO | WO-2014100036 A1 | 6/2014 |
| WO | WO-2014100687 A2 | 6/2014 |
| WO | WO-2014106056 A2 | 7/2014 |
| WO | WO-2014123846 A1 | 8/2014 |
| WO | WO-2014133822 A2 | 9/2014 |
| WO | WO-2014141221 A2 | 9/2014 |
| WO | WO-2014145496 A1 | 9/2014 |
| WO | WO-2014150255 A2 | 9/2014 |
| WO | WO-2014152963 A1 | 9/2014 |
| WO | WO-2014189070 A1 | 11/2014 |
| WO | WO-2014009876 A3 | 12/2014 |
| WO | WO-2015019273 A2 | 2/2015 |
| WO | WO-2015025482 A1 | 2/2015 |
| WO | WO-2015026387 A1 | 2/2015 |
| WO | WO-2015050816 A1 | 4/2015 |
| WO | WO-2015078112 A1 | 6/2015 |
| WO | WO-2015085249 A1 | 6/2015 |
| WO | WO-2015091070 A1 | 6/2015 |
| WO | WO-2015124670 A1 | 8/2015 |
| WO | WO-2015132528 A1 | 9/2015 |
| WO | WO-2015140801 A2 | 9/2015 |
| WO | WO-2015143099 A2 | 9/2015 |
| WO | WO-2015145455 A1 | 10/2015 |
| WO | WO-2015156143 A1 | 10/2015 |
| WO | WO-2015164787 A1 | 10/2015 |
| WO | WO-2015179915 A1 | 12/2015 |
| WO | WO-2015179916 A1 | 12/2015 |
| WO | WO-2015179917 A1 | 12/2015 |
| WO | WO-2015181836 A2 | 12/2015 |
| WO | WO-2015187480 A1 | 12/2015 |
| WO | WO-2016001088 A1 | 1/2016 |
| WO | WO-2016006536 A1 | 1/2016 |
| WO | WO-2016018448 A1 | 2/2016 |
| WO | WO-2016075656 A1 | 5/2016 |
| WO | WO-2016108163 A1 | 7/2016 |
| WO | WO-2016118318 A1 | 7/2016 |
| WO | WO-2016118330 A1 | 7/2016 |
| WO | WO-2016120820 A2 | 8/2016 |
| WO | WO-2016136694 A1 | 9/2016 |
| WO | WO-2016141799 A1 | 9/2016 |
| WO | WO-2016151364 A1 | 9/2016 |
| WO | WO-2016160849 A1 | 10/2016 |
| WO | WO-2016175649 A1 | 11/2016 |
| WO | WO-2016178936 A1 | 11/2016 |
| WO | WO-2016190978 A1 | 12/2016 |
| WO | WO-2017001848 A1 | 1/2017 |
| WO | WO-2017004423 A1 | 1/2017 |
| WO | WO-2017027729 A2 | 2/2017 |
| WO | WO-2017035024 A1 | 3/2017 |
| WO | WO-2017053384 A1 | 3/2017 |
| WO | WO-2017062042 A1 | 4/2017 |
| WO | WO-2017142100 A1 | 8/2017 |
| WO | WO-2017165895 A1 | 9/2017 |
| WO | WO-2017192673 A1 | 11/2017 |
| WO | WO-2018007100 A1 | 1/2018 |
| WO | WO-2018013666 A1 | 1/2018 |
| WO | WO-2018033819 A1 | 2/2018 |
| WO | WO-2018044894 A1 | 3/2018 |
| WO | WO-2018064234 A1 | 4/2018 |
| WO | WO-2018067593 A2 | 4/2018 |
| WO | WO-2018082813 A1 | 5/2018 |
| WO | WO-2018091492 A1 | 5/2018 |
| WO | WO-2018096390 A1 | 5/2018 |
| WO | WO-2018108724 A1 | 6/2018 |
| WO | WO-2018144056 A1 | 8/2018 |
| WO | WO-2018145880 A1 | 8/2018 |
| WO | WO-2018165049 A1 | 9/2018 |
| WO | WO-2018210693 A1 | 11/2018 |
| WO | WO-2018217605 A1 | 11/2018 |
| WO | WO-2019063462 A1 | 4/2019 |
| WO | WO-2019089118 A1 | 5/2019 |
| WO | WO-2019140441 A2 | 7/2019 |
| WO | WO-2019140444 A1 | 7/2019 |
| WO | WO-2019140448 A1 | 7/2019 |
| WO | WO-2019140449 A1 | 7/2019 |
| WO | WO-2020159677 A1 | 8/2020 |
| WO | WO-2020263508 A1 | 12/2020 |
| WO | WO-2022028723 A1 | 2/2022 |

OTHER PUBLICATIONS

Cinterion., "Cinterion PHS8-P 3G HSPA+," retrieved from http://www.cinterion.com/tl_files/cinterion/downloads/cinterion_datasheet_PHSS_web.pdf, 2012, 2 pages.
"Data Sheet—LuminOx O2 Sensors—Fluorescence-based Optical Series," SST Sensing Ltd., DS-0030 Rev 13, 2017, 2 pages.
Embedded Staff, "Understanding MCU Sleep Modes And Energy Savings," Mar. 6, 2012, XP055745374, Retrieved from the Internet: https://www.embedded.com/understanding-mcu-sleep-modes--and-energy-savings/, retrieved on Oct. 29, 2020, 11 pages.
International Search Report and Written Opinion for Application No. PCT/EP2020/072663, mailed on Feb. 8, 2021, 22 pages.
International Search Report and Written Opinion for Application No. PCT/EP2020/078551, mailed on Jan. 11, 2021, 13 pages.
Invitation to Pay Additional Fees and Partial Search Report for Application No. PCT/EP2020/072663, mailed on Nov. 19, 2020, 06 pages.
Ramachandran V.R. K., et al., "Potential of Wake-Up Radio-Based MAC Protocols for Implantable Body Sensor Networks (IBSN)—A Survey," Sensors, XP055769640., vol. 16, No. 12, Nov. 29, 2016. 31 pages.
Reinke P. et al., "Aerodynamics and Ventilation in Rail Tunnels," retrieved from https://www.tunneltalk.com/TunnelTECH-May2015-Aerodynamics-and-ventilation-in-rail-tunnels-civil-measures.php, TunnelTalk Direct by Design, May 2015, 6 pages.
Tomimatsu Y., et al., "A Wake-Up Switch using a Piezoelectric Differential Pressure Sensor," Intelligent Sensors, Sensor Networks and Information Processing, 2013 IEEE Eighth International Conference, XP032422506, Apr. 2, 2013, pp. 23-26.
Avery Dennison., "That's all you Need: One NFC Tag for Endless Applications," published on 2025, Retrieved from the Internet: https://rfid.averydennison.com/en/home/news-insights/insights/nfc-for-all.html (Year: 2025).
Orange., "What is the difference between NFC and RFID?," published on 2024, Retrieved from the Internet: https://iotjourney.orange.com/en/support/faq/what-is-the-difference-between-nfc-and-rfid (Year: 2024).
"Technical Overview", NFC Forum, 2024 (webpage accessed Sep. 11, 2024), 9 pages. Retrieved from the Internet: https://nfc-forum.org/learn/nfc-technology.
International Preliminary Report on Patentability for Application No. PCT/EP2020/072663, mailed on Feb. 24, 2022, 16 pages.
International Preliminary Report on Patentability for Application No. PCT/EP2020/078551, mailed on Apr. 28, 2022, 8 pages.

\* cited by examiner

SYSTEMS AND METHODS FOR MONITORING ESSENTIAL PERFORMANCE OF WOUND THERAPY

CROSS-REFERENCE TO RELATED APPLICATIONS

This application is a U.S. national stage application of International Patent Application No. PCT/EP2020/072663, filed Aug. 12, 2020, which claims priority to Great Britain Patent Application No. 1911693.8, filed Aug. 15, 2019, each of which is hereby incorporated by reference in its entirety and made part of this disclosure.

TECHNICAL FIELD

Embodiments described herein relate to apparatuses, systems, and methods the treatment of wounds, for example using dressings in combination with negative pressure wound therapy.

DESCRIPTION OF THE RELATED ART

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds, and abdominal wounds or the like. TNP therapy assists in the closure and healing of wounds by reducing tissue edema, encouraging blood flow, stimulating the formation of granulation tissue, removing excess exudates and may reduce bacterial load. Thus, reducing infection to the wound. Furthermore, TNP therapy permits less outside disturbance of the wound and promotes more rapid healing.

SUMMARY

A negative pressure wound therapy monitoring device can include a housing configured to be disposed or positioned in a fluid flow path connecting a wound covered by a wound dressing to a source of negative pressure of a negative pressure wound therapy device or at the wound. The device can include electronic circuitry at least partially enclosed by the housing. The electronic circuitry can include a sensor configured to monitor at least one parameter associated with delivery of negative pressure wound therapy by the negative pressure wound therapy device. The electronic circuitry can be configured to operate in a first power state in which the sensor periodically measures a value of the at least one parameter (or cause the sensor to periodically measure a value of the at least one parameter). The electronic circuitry can be configured to, in response to detecting that the value of the at least one parameter is outside an operational range, transition to a second power state and generate an indication of abnormal delivery of the negative pressure wound therapy (or in response to detecting that the value of the at least one parameter is outside an operational range, generate an indication of abnormal delivery of the negative pressure wound therapy). The indication can be configured to be detected by the negative pressure wound therapy device.

The therapy monitoring device of any of the preceding paragraphs and/or any of the therapy monitoring devices described herein can include one or more of the following features. The indication of abnormal delivery of the negative pressure wound therapy can include indication of at least one of a leak in the fluid flow path, an overpressure in the fluid flow path, or non-compliance with a duration of negative pressure wound therapy. The therapy monitoring device can include a power source configured to power the electronic circuitry. Less power can be consumed by the electronic circuitry in the first power state than in the second power state. The first power state can include a low power state during in which capacity of the power source is conserved. The electronic circuitry can be configured to transition to the low power state after generating the indication. The power source can include an electroactive polymer configured to generate power in response to one or more of application of negative pressure or loss of negative pressure. The indication can include at least one of an acoustic signal or an electromagnetic signal.

The therapy monitoring device of any of the preceding paragraphs and/or any of the therapy monitoring devices described herein can include one or more of the following features. The sensor can include at least one of a pressure sensor is configured to monitor negative pressure at the wound, an oxygen sensor configured to monitor oxygen concentration at the wound, or a moisture sensor configured to monitor moisture level at the wound. The pressure sensor can include a pressure switch configured to provide an indication in response to the value of the at least one parameter being outside the operational range. The housing can include a substantially elastic material enclosing a volume of gas. The sensor can include a pressure sensor configured to monitor increase in pressure associated with the delivery of negative pressure wound therapy. The housing can be configured to be positioned on or within the wound dressing or in a fluidic connector connecting the wound dressing to the source of negative pressure. The operational range can be associated with at least one of a minimum negative pressure level, a range of negative pressure, or a minimum duration of the negative pressure wound therapy over a period of time.

The therapy monitoring device of any of the preceding paragraphs and/or any of the therapy monitoring devices described herein can include one or more of the following features. The electronic circuitry can include a transmitter configured to transmit information. The electronic circuitry can be configured to operate in a standby state in which at least the transmitter is deactivated. The electronic circuitry can be configured to, in response to a detection of provision of negative pressure wound therapy, transition from the standby state to the first power state in which the transmitter is activated (or in response to a detection of provision of negative pressure wound therapy, activate the transmitter). The electronic circuitry can consume less power in the standby state than in the first power state. The sensor can include a pressure sensor. The electronic circuitry can be configured to detect provision of negative pressure wound therapy in response to a detection that pressure measured by the pressure sensor satisfies a pressure decrease threshold. The pressure decrease threshold can include a pressure difference threshold indicative of a differential pressure in the fluid flow path associated with provision of negative pressure wound therapy or a rate of pressure change threshold indicative of a rate of pressure decrease in the fluid flow path associated with provision of negative pressure wound therapy. The pressure decrease threshold can include the rate of pressure change threshold. The electronic circuitry can be configured to detect provision of negative pressure wound therapy in response to a detection that rate of pressure change determined from pressure measurements by the pressure sensor over a period of time satisfies the rate of pressure change threshold. The rate of pressure change threshold can be selected to distinguish provision of negative pressure wound therapy from a pressure decrease caused by transporting the device by aircraft or train.

The therapy monitoring device of any of the preceding paragraphs and/or any of the therapy monitoring devices described herein can include one or more of the following features. The electronic circuitry can be configured to, subsequent to the transition from the standby state to the first power state, attempt to pair via the transmitter with the negative pressure wound therapy device. The electronic control circuitry can be configured to, in response to being unable to pair, transition to the standby state. The electronic circuitry can be configured to transition to the standby state subsequent to expiration of a duration of time over which the electronic circuitry attempts to pair. The electronic circuitry can be configured to transition to the standby state in response to receiving an indication that provision of negative pressure wound therapy has been stopped. The indication can be transmitted by the negative pressure wound therapy device.

A fluidic connector for connecting a negative pressure wound therapy device to a wound can support the therapy monitoring device of any of the preceding paragraphs and/or any of the therapy monitoring devices described herein. A wound dressing can support the therapy monitoring device of any of the preceding paragraphs and/or any of the therapy monitoring devices described herein.

A negative pressure wound therapy system can include a negative pressure wound therapy device including a negative pressure source configured to be fluidically connected via a fluid flow path to a wound dressing positioned over a wound. The negative pressure source can be configured to provide negative pressure therapy to the wound via the fluid flow path. The negative pressure wound therapy device can include a controller. The system can include a therapy monitoring device configured to be disposed or positioned in the fluid flow path or at the wound. The therapy monitoring device can be configured to monitor a parameter associated with the provision of negative pressure wound therapy and generate a first signal in response to detecting that a value of the parameter is outside an operational range. The controller can be configured to detect the first signal generated by the therapy monitoring device. The controller can be configured to verify that the therapy monitoring device is paired with the negative pressure wound therapy device. The controller can be configured to, in response to the verification, determine if the negative pressure source has been activated to provide negative pressure to the wound. The controller can be configured to, in response to the determination that the negative pressure source has been activated, generate an alarm associated with the first signal.

The negative pressure wound therapy system of any of the preceding paragraphs and/or any of the negative pressure wound therapy systems described herein can include one or more of the following features. The controller can be configured to detect a second signal generated by the therapy monitoring device. The second signal can include a pressure measured by the therapy monitoring device at a time when the negative pressure source is not active. The controller can be configured to pair the negative pressure wound therapy device with the therapy monitoring device in response to verifying that the pressure measured by the therapy monitoring device at the time when the negative pressure source is not active is zero. The second signal can include a code. The controller can be configured to pair the negative pressure wound therapy device with the therapy monitoring device in response to verifying the code. The controller can be configured to pair the negative pressure wound therapy device with the therapy monitoring device in response to one or more of: causing the negative pressure source to deliver at least one negative pressure pulse via the fluid flow path, receiving a third signal including a pressure measured by the therapy monitoring device, or verifying that the pressure measured by the therapy monitoring device matches the at least one negative pressure pulse. At least one negative pressure pulse can include a set of negative pressure pulses. The set of negative pressure pulses can be delivered according to at least one of a step function, triangular function, trapezoidal function, sawtooth function, or sinusoidal function.

The negative pressure wound therapy system of any of the preceding paragraphs and/or any of the negative pressure wound therapy systems described herein can include one or more of the following features. The therapy monitoring device can be configured to operate in a first power mode in which the therapy monitoring device periodically measures the value of the parameter. The therapy monitoring device can be configured to, in response to detecting that the value of the parameter is outside the operational range, transition to a second power mode and generate the first signal. First power mode can be a low power mode during in which capacity of a power source of the therapy monitoring device is conserved. The therapy monitoring device can be configured to transition to the low power mode after generating the first signal. Operational range can be associated with at least one of a minimum negative pressure level, a range of negative pressure, or a minimum duration of the negative pressure wound therapy over a period of time.

A negative pressure wound therapy device can include a negative pressure source configured to provide, via a fluid flow path, negative pressure to a wound covered by a wound dressing. The device can include a controller. The controller can be configured to detect an indication generated by a therapy monitoring device positioned in the fluid flow path in response to the therapy monitoring device detecting that a parameter associated with the provision of negative pressure is outside an operational range. The controller can be configured to, in response to the detection of the indication and a determination that the negative pressure source has been activated to provide negative pressure to the wound, generate an alarm indicative of abnormal provision of negative pressure.

The negative pressure wound therapy device of any of the preceding paragraphs and/or any of the negative pressure wound therapy device described herein can include one or more of the following features. The controller can be configured to, in response to the detection of the indication and a determination that the negative pressure source has been activated to provide negative pressure in an intermittent mode (which can include cycling between provision of negative pressure at first and second negative pressure levels), generate a first alarm in response to determining that the indication has been detected at a time during which the negative pressure source is not operating to supply negative pressure at the first negative pressure level. The first alarm can be indicative of a leak in the fluid flow path. The controller can be configured to, in response to the detection of the indication and the determination that the negative pressure source has been activated to provide negative pressure in the intermittent mode, generate a second alarm in response to determining that the indication has been detected at a time during which the negative pressure source is not operating to supply negative pressure at the second negative pressure level. The second alarm can be indicative of an overpressure in the fluid flow path.

The negative pressure wound therapy device of any of the preceding paragraphs and/or any of the negative pressure wound therapy device described herein can include one or more of the following features. The controller can be configured to verify that the therapy monitoring device is paired with the negative pressure wound therapy device by one or more of: causing the negative pressure source to deliver a set of negative pressure pulses to the wound via the fluid flow path, receiving a signal indicating pressure measured by the therapy monitoring device, or determining that the signal indicating pressure measured by the therapy monitoring device corresponds to the set of negative pressure pulses. The controller can be configured to generate the alarm based on the verification that the therapy monitoring device is paired with the negative pressure wound therapy device. Operational range can be associated with at least one of a minimum negative pressure level, a range of negative pressure, or a minimum duration of the negative pressure wound therapy over a period of time.

A negative pressure wound therapy monitoring device can include a housing configured to be disposed in a fluid flow path connecting a wound covered by a wound dressing to a source of negative pressure of a negative pressure wound therapy device. The therapy monitoring device can include a pressure sensor at least partially enclosed by the housing, the pressure sensor configured to measure pressure at the wound. The therapy monitoring device can include electronic control circuitry at least partially enclosed by the housing. The electronic control circuitry can be in communication with the pressure sensor. The electronic circuitry can be configured to operate in a first power state in which the pressure sensor periodically measures pressure in the fluid flow path. The electronic circuitry can be configured to, in response to detecting that pressure measured by the pressure sensor is outside an operational range, transition to a second power state and generate a signal configured to be detected by the negative pressure wound therapy device, the signal indicative of a detection of an operating condition.

The therapy monitoring device of any of the preceding paragraphs and/or any of the therapy monitoring devices described herein can include one or more of the following features. Operating condition can include at least one of a leak in the fluid flow path, an overpressure in the fluid flow path, the overpressure indicative of an unsafe level of negative pressure in the fluid flow path, or non-compliance with a duration of negative pressure wound therapy. Less power can be consumed in the first power state than in the second power state. The signal can include at least one of an acoustic signal or an electromagnetic signal. The signal can include an acoustic signal with frequency above the human hearing range. The pressure sensor can be configured to measure pressure at the wound.

The therapy monitoring device of any of the preceding paragraphs and/or any of the therapy monitoring devices described herein can include one or more of the following features. The monitoring device can be associated with an identification code. The identification code can be used for pairing the monitoring device with the negative pressure wound therapy device. At least one of the electronic control circuitry or the pressure sensor can be powered by an electroactive polymer configured to generate electrical power in response to one or more of application of negative pressure or loss of negative pressure. The therapy monitoring device can include a power source at least partially enclosed by the housing and configured to supply power to at least one of the pressure sensor and the electronic control circuitry. The first power state can be a low power state during in which capacity of the power source is conserved. The electronic control circuitry can be configured to transition to the low power state after generating the signal. The housing can be configured to be positioned on or within the wound dressing or in a fluidic connector connecting the wound dressing to the source of negative pressure.

A negative pressure wound therapy system can include a negative pressure wound therapy device including a negative pressure source configured to be fluidically connected via a fluid flow path to a wound dressing positioned over a wound. The negative pressure source can be configured to provide negative pressure therapy to the wound via the fluid flow path. The negative pressure wound therapy device can include a controller. The negative pressure wound therapy system can include a therapy monitoring device configured to be disposed in the fluid flow path. The therapy monitoring device can be configured to measure pressure under the wound dressing and generate a first signal in response to detecting that pressure under the wound dressing is outside an operational range. The controller can be configured to detect the first signal generated by the therapy monitoring device. The controller can be configured to verify that the therapy monitoring device is paired with the negative pressure wound therapy device. The controller can be configured to, in response to the verification, determine if the negative pressure source has been activated to provide negative pressure to the wound. The controller can be configured to, in response to the verification and in response to the determination that the negative pressure source has been activated, generate an indication of detection of an operating condition associated with the first signal.

The negative pressure wound therapy system of any of the preceding paragraphs and/or any of the negative pressure wound therapy systems described herein can include one or more of the following features. The controller can be configured to detect a second signal generated by the therapy monitoring device. The second signal can include a pressure measured by the therapy monitoring device at a time when the negative pressure source is not active. The controller can be configured to pair the negative pressure wound therapy device with the monitoring device in response to verifying that the pressure measured by the therapy monitoring device at the time when the negative pressure source is not active is zero. The second signal can include a code. The controller can be configured to pair the negative pressure wound therapy device with the therapy monitoring device in response to verifying the code. The controller can be configured to pair the negative pressure wound therapy device with the therapy monitoring device in response to one or more of: causing the negative pressure source to deliver at least one negative pressure pulse via the fluid flow path, receiving a third signal including a pressure measured by the therapy monitoring device, or verifying that the pressure measured by the monitoring device matches the at least one negative pressure pulse. At least one negative pressure pulse can include a set of negative pressure pulses. The set of negative pressure pulses can be delivered as at least one of a step function, triangular function, trapezoidal function, sawtooth function, or sinusoidal function.

The negative pressure wound therapy system of any of the preceding paragraphs and/or any of the negative pressure wound therapy systems described herein can include one or more of the following features. Operating condition can include at least one of a leak in the fluid flow path, an overpressure in the fluid flow path, or non-compliance with a duration of negative pressure wound therapy. The therapy monitoring device can be configured to operate in a first power mode in which the monitoring device periodically measures pressure in the fluid flow path. The therapy monitoring device can be configured to, in response to detecting that pressure measured by the therapy monitoring device is outside the operational range, transition to a second power mode and generate the first signal. The first power mode can be a low power mode during in which capacity of a power source of the therapy monitoring device is conserved. The therapy monitoring device can be configured to transition to the low power mode after generating the first signal.

A negative pressure wound therapy device can include a negative pressure source configured to provide negative pressure, via a flow path, to a wound covered by a wound dressing. The negative pressure wound therapy device can include a controller. The controller can be configured to detect a first signal generated by a therapy monitoring device positioned in the fluid flow path in response to the therapy monitoring device detecting that pressure at the wound is outside an operational range. The controller can be configured to, in response to the detection of the first signal and a determination that the negative pressure source has been activated to provide negative pressure to the wound, generate an indication of detecting an operating condition associated with the first signal.

The negative pressure wound therapy device of any of the preceding paragraphs and/or any of the negative pressure wound therapy device described herein can include one or more of the following features. Operating condition can include at least one of a leak in the fluid flow path, an overpressure in the fluid flow path, or non-compliance with a duration of negative pressure wound therapy. The controller can be configured to, in response to the detection of the first signal and a determination that the negative pressure source has been activated to provide negative pressure in a cyclical mode (which can include providing the negative pressure at low and high negative pressure levels), generate a first indication in response to determining that the first signal has been detected at a time during which the negative pressure source is not operating to supply negative pressure at the low negative pressure level. The first indication can be associated with a leak in the fluid flow path. The controller can be configured to, in response to the detection of the first signal and the determination that the negative pressure source has been activated to provide negative pressure in the cyclical mode, generate a second indication in response to determining that the first signal has been detected at a time during which the negative pressure source is not operating to supply negative pressure at the high negative pressure level. The second indication can be associated with an overpressure in the fluid flow path.

The negative pressure wound therapy device of any of the preceding paragraphs and/or any of the negative pressure wound therapy device described herein can include one or more of the following features. The controller can be configured to verify that the therapy monitoring device is paired with the negative pressure wound therapy device by one or more of: causing the negative pressure source to deliver a set of negative pressure pulses to the wound via the fluid flow path, receiving a second signal indicating pressure measured by the therapy monitoring device, or determining that the second signal indicating pressure measured by the therapy monitoring device corresponds to the set of negative pressure pulses. The controller can be configured to generate the indication based on the verification that the therapy monitoring device is paired with the negative pressure wound therapy device.

A negative pressure wound therapy monitoring device can include a housing configured to be disposed in a fluid flow path connecting a wound covered by a wound dressing to a source of negative pressure of a negative pressure wound therapy device. The therapy monitoring device can include a pressure sensor at least partially enclosed by the housing, the pressure sensor configured to measure pressure at the wound. The therapy monitoring device can include electronic control circuitry at least partially enclosed by the housing. The electronic control circuitry can be in communication with the pressure sensor. The electronic circuitry can be configured to operate in a first power state in which the pressure sensor periodically measures pressure in the fluid flow path. The electronic circuitry can be configured to, in response to detecting that pressure measured by the pressure sensor is outside an operational range, transition to a second power state and generate a signal configured to be detected by the negative pressure wound therapy device, the signal indicative of a detection of an operating condition.

The therapy monitoring device of any of the preceding paragraphs and/or any of the therapy monitoring devices described herein can include one or more of the following features. Operating condition can include at least one of a leak in the fluid flow path, an overpressure in the fluid flow path, the overpressure indicative of an unsafe level of negative pressure in the fluid flow path, or non-compliance with a duration of negative pressure wound therapy. Less power can be consumed in the first power state than in the second power state. The signal can include at least one of an acoustic signal or an electromagnetic signal. The signal can include an acoustic signal with frequency above the human hearing range. The pressure sensor can be configured to measure pressure at the wound.

The therapy monitoring device of any of the preceding paragraphs and/or any of the therapy monitoring devices described herein can include one or more of the following features. The monitoring device can be associated with an identification code. The identification code can be used for pairing the monitoring device with the negative pressure wound therapy device. At least one of the electronic control circuitry or the pressure sensor can be powered by an electroactive polymer configured to generate electrical power in response to one or more of application of negative pressure or loss of negative pressure. The therapy monitoring device can include a power source at least partially enclosed by the housing and configured to supply power to at least one of the pressure sensor and the electronic control circuitry. The first power state can be a low power state during in which capacity of the power source is conserved. The electronic control circuitry can be configured to transition to the low power state after generating the signal. The housing can be configured to be positioned on or within the wound dressing or in a fluidic connector connecting the wound dressing to the source of negative pressure.

A negative pressure wound therapy system can include a negative pressure wound therapy device including a negative pressure source configured to be fluidically connected via a fluid flow path to a wound dressing positioned over a wound. The negative pressure source can be configured to provide negative pressure therapy to the wound via the fluid flow path. The negative pressure wound therapy device can include a controller. The negative pressure wound therapy system can include a therapy monitoring device configured to be disposed in the fluid flow path. The therapy monitoring device can be configured to measure pressure under the wound dressing and generate a first signal in response to detecting that pressure under the wound dressing is outside an operational range. The controller can be configured to detect the first signal generated by the therapy monitoring device. The controller can be configured to verify that the therapy monitoring device is paired with the negative pressure wound therapy device. The controller can be configured to, in response to the verification, determine if the negative pressure source has been activated to provide negative pressure to the wound. The controller can be configured to, in response to the verification and in response to the determination that the negative pressure source has been activated, generate an indication of detection of an operating condition associated with the first signal.

The negative pressure wound therapy system of any of the preceding paragraphs and/or any of the negative pressure wound therapy systems described herein can include one or more of the following features. The controller can be configured to detect a second signal generated by the therapy monitoring device. The second signal can include a pressure measured by the therapy monitoring device at a time when the negative pressure source is not active. The controller can be configured to pair the negative pressure wound therapy device with the monitoring device in response to verifying that the pressure measured by the therapy monitoring device at the time when the negative pressure source is not active is zero. The second signal can include a code. The controller can be configured to pair the negative pressure wound therapy device with the therapy monitoring device further in response to verifying the code. The controller can be configured to pair the negative pressure wound therapy device with the therapy monitoring device in response to one or more of: causing the negative pressure source to deliver at least one negative pressure pulse via the fluid flow path, receiving a third signal including a pressure measured by the therapy monitoring device, or verifying that the pressure measured by the monitoring device matches the at least one negative pressure pulse. At least one negative pressure pulse can include a set of negative pressure pulses. The set of negative pressure pulses can be delivered as at least one of a step function, triangular function, trapezoidal function, sawtooth function, or sinusoidal function.

The negative pressure wound therapy system of any of the preceding paragraphs and/or any of the negative pressure wound therapy systems described herein can include one or more of the following features. Operating condition can include at least one of a leak in the fluid flow path, an overpressure in the fluid flow path, or non-compliance with a duration of negative pressure wound therapy. The therapy monitoring device can be configured to operate in a first power mode in which the monitoring device periodically measures pressure in the fluid flow path. The therapy monitoring device can be configured to, in response to detecting that pressure measured by the therapy monitoring device is outside the operational range, transition to a second power mode and generate the first signal. The first power mode can be a low power mode during in which capacity of a power source of the therapy monitoring device is conserved. The therapy monitoring device can be configured to transition to the low power mode after generating the first signal.

A negative pressure wound therapy device can include a negative pressure source configured to provide negative pressure, via a flow path, to a wound covered by a wound dressing. The negative pressure wound therapy device can include a controller. The controller can be configured to detect a first signal generated by a therapy monitoring device positioned in the fluid flow path in response to the therapy monitoring device detecting that pressure at the wound is outside an operational range. The controller can be configured to, in response to the detection of the first signal and a determination that the negative pressure source has been activated to provide negative pressure to the wound, generate an indication of detecting an operating condition associated with the first signal.

The negative pressure wound therapy device of any of the preceding paragraphs and/or any of the negative pressure wound therapy device described herein can include one or more of the following features. Operating condition can include at least one of a leak in the fluid flow path, an overpressure in the fluid flow path, or non-compliance with a duration of negative pressure wound therapy. The controller can be configured to, in response to the detection of the first signal and a determination that the negative pressure source has been activated to provide negative pressure in a cyclical mode (which can include providing the negative pressure at low and high negative pressure levels), generate a first indication in response to determining that the first signal has been detected at a time during which the negative pressure source is not operating to supply negative pressure at the low negative pressure level. The first indication can be associated with a leak in the fluid flow path. The controller can be configured to, in response to the detection of the first signal and the determination that the negative pressure source has been activated to provide negative pressure in the cyclical mode, generate a second indication in response to determining that the first signal has been detected at a time during which the negative pressure source is not operating to supply negative pressure at the high negative pressure level. The second indication can be associated with an overpressure in the fluid flow path.

The negative pressure wound therapy device of any of the preceding paragraphs and/or any of the negative pressure wound therapy device described herein can include one or more of the following features. The controller can be configured to verify that the therapy monitoring device is paired with the negative pressure wound therapy device by one or more of: causing the negative pressure source to deliver a set of negative pressure pulses to the wound via the fluid flow path, receiving a second signal indicating pressure measured by the therapy monitoring device, or determining that the second signal indicating pressure measured by the therapy monitoring device corresponds to the set of negative pressure pulses. The controller can be configured to generate the indication further based on the verification that the therapy monitoring device is paired with the negative pressure wound therapy device.

A pressure monitor for negative pressure wound therapy can include a pressure sensor configured to be positioned in a fluid flow path connecting a wound to a negative pressure wound therapy device or at the wound. The pressure sensor can be configured to measure pressure in the fluid flow path or at the wound. The monitor can include communication circuitry configured to transmit data to the negative pressure wound therapy device. The communication circuitry can be configured to operate in an inactive state in which the communication circuitry is not configured to transmit data. The communication circuitry can be configured to operate in an active state in which the communication circuitry is configured to transmit data. The monitor can include a power source configured to supply electrical power to the pressure sensor and the communication circuitry. The monitor can include control circuitry. The control circuitry can be configured to, in response to determining that a decrease in pressure measured by the pressure sensor satisfies a pressure decrease threshold indicative of negative pressure therapy being applied to the wound by a negative pressure source of the negative pressure wound therapy device, cause the communication circuitry to be in the active state and cause the communication circuitry to periodically transmit wound pressure measured by the pressure sensor to the negative pressure wound therapy device. The control circuitry can be configured to, in response to determining that the decrease in pressure in the wound measured by the pressure sensor does not satisfy the pressure decrease threshold, cause the communication circuitry to be in the inactive state to conserve capacity of the power source.

The monitor of any of the preceding paragraphs and/or any of the monitors described herein can include one or more of the following features. The communication circuitry can include a transceiver configured to wirelessly transmit data. The monitor can include a housing configured to at least partially support one or more of the pressure sensor, the communication circuitry, the power source, or the control circuitry. The housing can be configured to be at least one of: supported at least partially by a wound dressing configured to cover the wound, supported at least partially by a fluidic connector configured to connect the wound to the negative pressure wound therapy device, or positioned under the wound dressing.

The monitor of any of the preceding paragraphs and/or any of the monitors described herein can include one or more of the following features. The pressure decrease threshold comprises a pressure difference threshold indicative of a differential pressure in the fluid flow path associated with application of negative pressure wound therapy or a rate of pressure change threshold indicative of a rate of pressure decrease in the fluid flow path associated with application of negative pressure wound therapy. The pressure decrease threshold can include the rate of pressure change threshold. The control circuitry can be configured to determine whether a rate of decrease in pressure measured by the pressure sensor over a period of time satisfies the rate of pressure change threshold. The rate of pressure change threshold can be selected to distinguish application of negative pressure wound therapy from a pressure decrease caused by transporting the monitor by aircraft or train.

The monitor of any of the preceding paragraphs and/or any of the monitors described herein can include one or more of the following features. The control circuitry can be configured to, subsequent to causing the communication circuitry to be in the active state, attempt to pair via the communication circuitry with the negative pressure wound therapy device. The control circuitry can be configured to, in response to being unable to pair, cause the communication circuitry to be in the inactive state. The control circuitry can be configured to cause the communication circuitry to be in the inactive state subsequent to expiration of a duration of time over which the control circuitry attempts to pair. The control circuitry can be configured to cause the communication circuitry to be in the inactive state in response to receiving an indication that application of negative pressure wound therapy has been stopped. The indication can be transmitted by the negative pressure wound therapy device.

A fluidic connector for connecting a negative pressure wound therapy device to a wound can support the pressure monitor of any of the preceding paragraphs and/or any of the pressure monitors described herein. A wound dressing can support the pressure monitor of any of the preceding paragraphs and/or any of the pressure monitors described herein.

Disclosed are methods of operating the therapy monitoring device, the negative pressure wound therapy device, the negative pressure wound therapy system, and/or the pressure monitor of described in any of the preceding paragraphs and/or elsewhere herein.

Any of the features, components, or details of any of the arrangements or embodiments disclosed in this application, including without limitation any of the apparatus embodiments and any of the negative pressure wound therapy embodiments disclosed herein, are interchangeably combinable with any other features, components, or details of any of the arrangements or embodiments disclosed herein to form new arrangements and embodiments.

DETAILED DESCRIPTION

Figure 1:
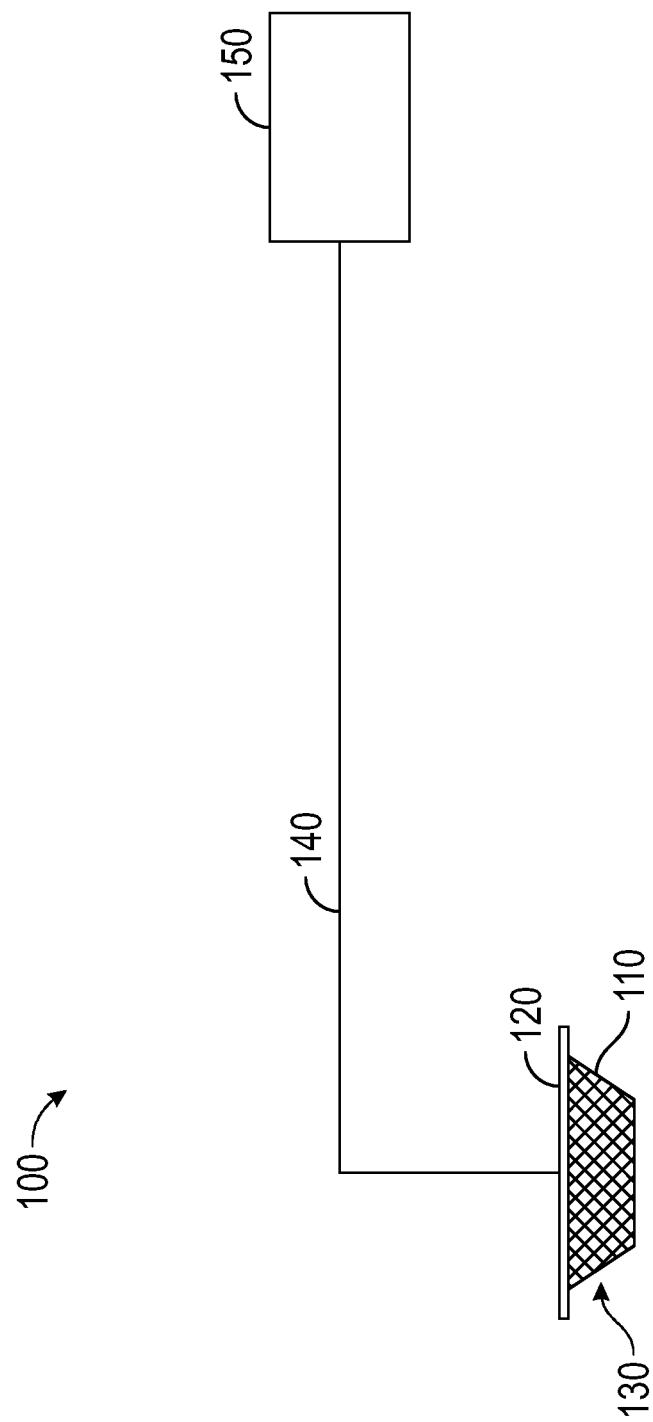
FIG. 1 illustrates a reduced pressure wound therapy system.

Embodiments disclosed herein relate to systems and methods of monitoring and/or treating a wound. It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sternotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Embodiments of systems and methods disclosed herein can be used with topical negative pressure ("TNP") or reduced pressure therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid. TNP therapy can help to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects pressure that is X mmHg below 760 mmHg or, in other words, a pressure of (760−X) mmHg. In addition, negative pressure that is "less" or "smaller" than X mmHg corresponds to pressure that is closer to atmospheric pressure (for example, −40 mmHg is less than −60 mmHg). Negative pressure that is "more" or "greater" than —X mmHg corresponds to pressure that is further from atmospheric pressure (for example, −80 mmHg is more than −60 mmHg). In some cases, local ambient atmospheric pressure is used as a reference point, and such local atmospheric pressure may not necessarily be, for example, 760 mmHg.

Systems and methods disclosed herein can be used with other types of treatment in addition to or instead of reduced pressure therapy, such as irrigation, ultrasound, heat and/or cold, neuro stimulation, or the like. In some cases, disclosed systems and methods can be used for wound monitoring without application of additional therapy. Systems and methods disclosed herein can be used in conjunction with a dressing, including with compression dressing, reduced pressure dressing, or the like.

A healthcare provider, such as a clinician, nurse, or the like, can provide a TNP prescription specifying, for example, the pressure level and/or time of application. However, the healing process is different for each patient and the prescription may affect the healing process in a way the clinician or healthcare provider did not expect at the time of devising the prescription. A healthcare provider may try to adjust the prescription as the wound heals (or does not heal), but such process may require various appointments that can be time consuming and repetitive. Embodiments disclosed herein provide systems, devices, and/or methods of efficiently adjusting TNP prescriptions and delivering effective TNP therapy.

Negative Pressure System

FIG. 1 illustrates a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. With any of the systems disclosed herein, as is illustrated in FIG. 1, a negative pressure wound therapy device (sometimes as a whole or partially referred to as a "pump assembly") can be a canisterless (meaning that exudate is collected in the wound dressing or is transferred via tube 140 for collection to another location). However, any of the pump assemblies disclosed herein can be configured to include or support a canister. Additionally, with any of the systems disclosed herein, any of the pump assemblies can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. In some cases, the wound cover 120 has a top side and a bottom side, and the bottom side adhesively (or in any other suitable manner) seals with wound cavity 110. The conduit 140 or any other conduit disclosed herein can be formed from polyurethane, PVC, nylon, polyethylene, silicone, or any other suitable material.

The wound cover 120 can have a port (not shown) configured to receive an end of the conduit 140. In some cases, the conduit 140 can otherwise pass through and/or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway or path between the pump assembly 150 and the wound cover 120, so as to supply the reduced pressure provided by the pump assembly 150 to wound cavity 110.

The wound cover 120 and the wound filler 130 can be provided as a single article or an integrated single unit. In some cases, no wound filler is provided and the wound cover by itself may be considered the wound dressing. The wound dressing may then be connected, via the conduit 140, to a source of negative pressure, such as the pump assembly 150. In some cases, though not required, the pump assembly 150 can be miniaturized and portable, although larger conventional pumps such can also be used.

The wound cover 120 can be located over a wound site to be treated. The wound cover 120 can form a substantially sealed cavity or enclosure over the wound site. In some cases, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some cases, the components of the TNP system described herein can be particularly suited for incisional wounds that exude a small amount of wound exudate.

The system can be designed to operate without the use of an exudate canister. The system can be configured to support an exudate canister. In some cases, configuring the pump assembly 150 and tubing 140 so that the tubing 140 can be quickly and easily removed from the pump assembly 150 can facilitate or improve the process of dressing or pump changes, if necessary. Any of the pump assemblies disclosed herein can be configured to have any suitable connection between the tubing and the pump.

The pump assembly 150 can be configured to deliver negative pressure of approximately −80 mmHg, or between about −20 mmHg and −200 mmHg. Note that these pressures are relative to normal ambient atmospheric pressure thus, −200 mmHg would be about 560 mmHg in practical terms. In some cases, the pressure range can be between about −40 mmHg and −150 mmHg. Alternatively a pressure range of up to −75 mmHg, up to −80 mmHg or over −80 mmHg can be used. Also in some cases a pressure range of below −75 mmHg can be used. Alternatively a pressure range of over approximately −100 mmHg, or even 150 mmHg, can be supplied by the pump assembly 150.

The pump assembly 150 can be configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure set points. Low set point can be set at above 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High set point can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some cases, switching between low and high set points and vice versa can be performed according to a step waveform, square waveform, sinusoidal waveform, and the like.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (such as, wound exudate) is drawn through the conduit 140, and can be stored in a canister. In some cases, fluid is absorbed by the wound filler 130 or one or more absorbent layers (not shown).

Wound dressings that may be utilized with the pump assembly and systems of the present application include Renasys-F, Renasys-G, Renasys AB, and Pico Dressings available from Smith & Nephew. Further description of such wound dressings and other components of a negative pressure wound therapy system that may be used with the pump assembly and systems of the present application are found in U.S. Patent Publication Nos. 2012/0116334, 2011/0213287, 2011/0282309, 2012/0136325 and U.S. Pat. No. 9,084,845, each of which is incorporated by reference in its entirety. In some cases, other suitable wound dressings can be utilized.

Pump Assembly and Canister

Figure 2A:
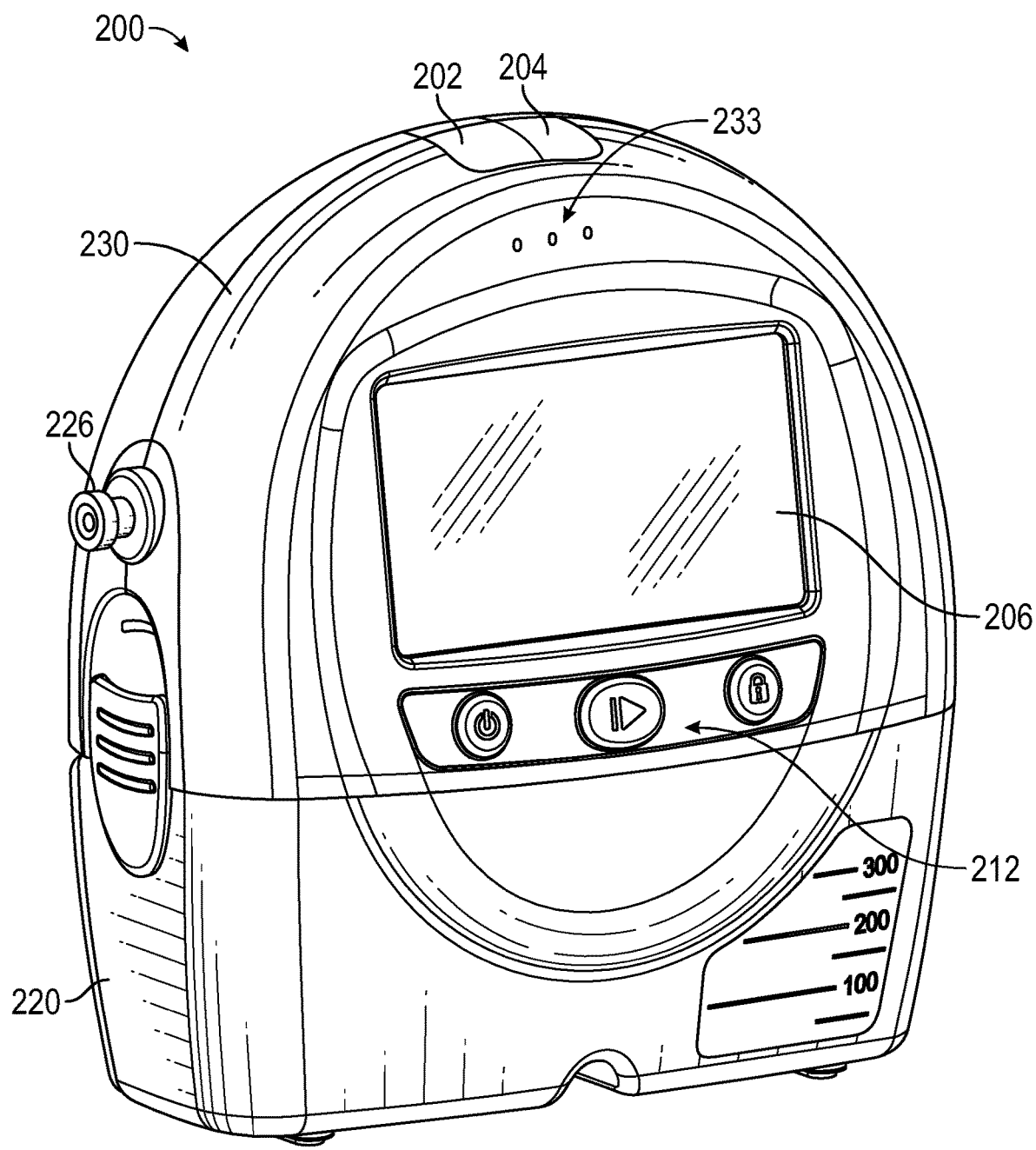
FIGS. 2A-2B illustrate a pump assembly and canister.
Figure 2B:
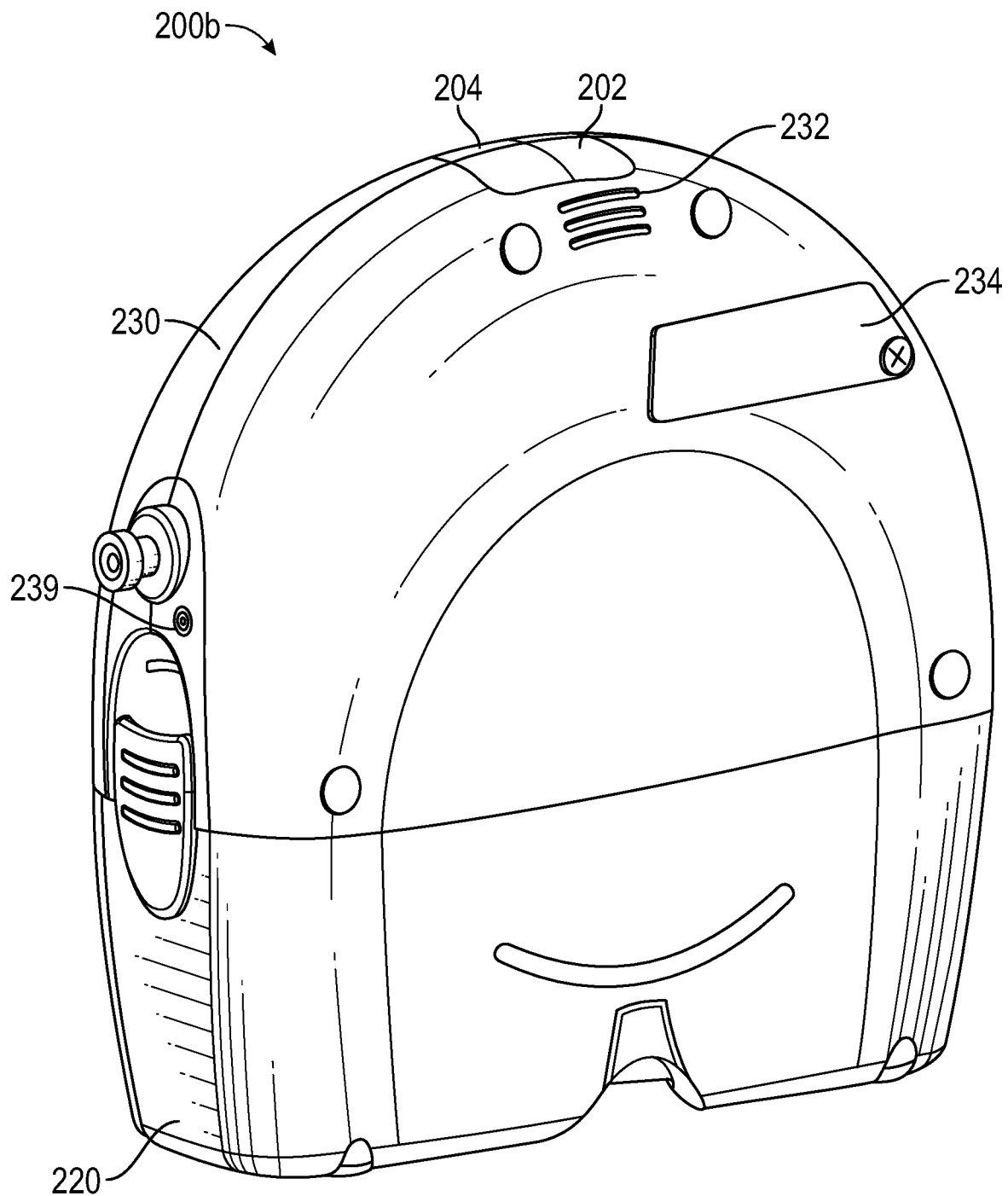

FIGS. 2A-B illustrates a negative pressure wound therapy device 200 including a pump assembly 230 and canister 220. As is illustrated, the pump assembly 230 and the canister are connected, thereby forming the device 200. The pump assembly 230 comprises one or more indicators, such as visual indicator 202 configured to indicate alarms and visual indicator 204 configured to indicate status of the TNP system. The indicators 202 and 204 can be configured to alert a user to a variety of operating and/or failure conditions of the system, including alerting the user to normal or proper operating conditions, pump failure, power supplied to the pump or power failure, detection of a leak within the wound cover or flow pathway (sometimes referred to as fluid flow path), suction blockage in the flow pathway, canister full, overpressure, or any other similar or suitable conditions or combinations thereof. In some cases, any one or more of the indicators 202 and 204 can be configured to alert a user that the current operation is compliant or non-compliant with a therapy prescription, which can be stored in a remote computing device (sometimes referred to a "remote computing system" or "remote computer"). The remote computing device can be any one or more computing devices with at least one processor and/or database, such as one or more cloud servers (sometimes referred to as "the cloud"). In some cases, the pump assembly 230 can comprise additional indicators. In some cases, a single indicator is used. In some cases, multiple indicators are used. Any one or more suitable indicators can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 comprises a display or screen 206 mounted in a recess formed in a case of the pump assembly. In some cases, the display 206 can be a touch screen display. In some cases, the display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion formed in the case of the pump assembly. The gripping portion can be configured to assist the user to hold the pump assembly 230, such as during removal of the canister 220. The pump assembly 230 includes one or more strap mounts for connecting a carry strap to the pump assembly 230 or for attaching a cradle. In some cases, the canister 220 can be replaced with another canister, such as when the canister 220 has been filled with fluid.

The pump assembly 230 comprises one or more keys or buttons 212 configured to allow the user to operate and monitor the operation of the TNP system. As is illustrated, there can be a plurality of buttons. One button can be configured as a power button to turn on/off the pump assembly 230. Another button can be configured as a play/pause button for the delivery of negative pressure therapy. For example, pressing the button can cause therapy to start, and pressing the button afterward can cause therapy to pause or end. A button can be configured to lock the display 206 and/or the buttons 212. For instance, a button can be pressed so that the user does not unintentionally alter the delivery of the therapy. In some cases, multiple key presses and/or sequences of key presses can be used to operate the pump assembly 230.

In some cases, the pump assembly 230 comprises a microphone 233 for detecting sound. The microphone 233 can be configured to detect signals from a therapy monitoring device as described in herein. The microphone 233 can be configured to receive specific frequencies of signals. For example, the microphone 233 can be configured to receive signals of 20 kHz or higher so that a high frequency signal generated by a therapy monitoring device but exclude acoustic signals generated by ambient noise or human voice. In some cases, the microphone 233 is disposed on the pump assembly 230 near the conduit 140 so that the microphone 233 can detect signals generated in the conduit.

The canister 220 is configured to hold fluid (such as, exudate) removed from the wound cavity 110. The canister 220 includes one or more latches for attaching the canister to the pump assembly 230. The exterior of the canister 220 can formed from frosted plastic so that the canister is substantially opaque and the contents of the canister and substantially hidden from plain view. The canister 220 includes a substantially transparent window, which can also include graduations of volume. For example, the illustrated 300 mL canister 220 includes graduations of 50 mL, 100 mL, 150 mL, 200 mL, 250 mL, and 300 mL. In some cases, the canister can hold different volume of fluid and can include different graduation scale. The canister 220 comprises a tubing channel for connecting to the conduit 140.

FIG. 2B illustrates a rear view 200B of the pump assembly 230 and canister 220. The pump assembly 230 comprises a speaker 232 for producing sound. The speaker 232 can be used to generate an acoustic alarm in response to deviations in therapy delivery, non-compliance with therapy delivery, or any other similar or suitable conditions or combinations thereof. The speaker 232 can be used to generate audio feedback to user input. The speaker 232 can be configured in a microphone mode (or include a microphone).

The pump assembly 230 can include a filter access door 234 for accessing and replacing one or more filters, such as antibacterial filters. The pump assembly 230 can comprise a power jack 239 for charging and recharging an internal battery of the pump assembly. In some cases, the power jack 239 is a direct current (DC) jack. In some cases, the pump assembly can comprise a disposable power source, such as batteries, so that no power jack is needed. In some cases, one of the power supplies (primary) can deliver power to operate and control the pump. In some cases, a secondary power source can deliver power to one or more of the user interface, alert system, and/or communication system for uploading usage data to the cloud.

Control System

Figure 3:
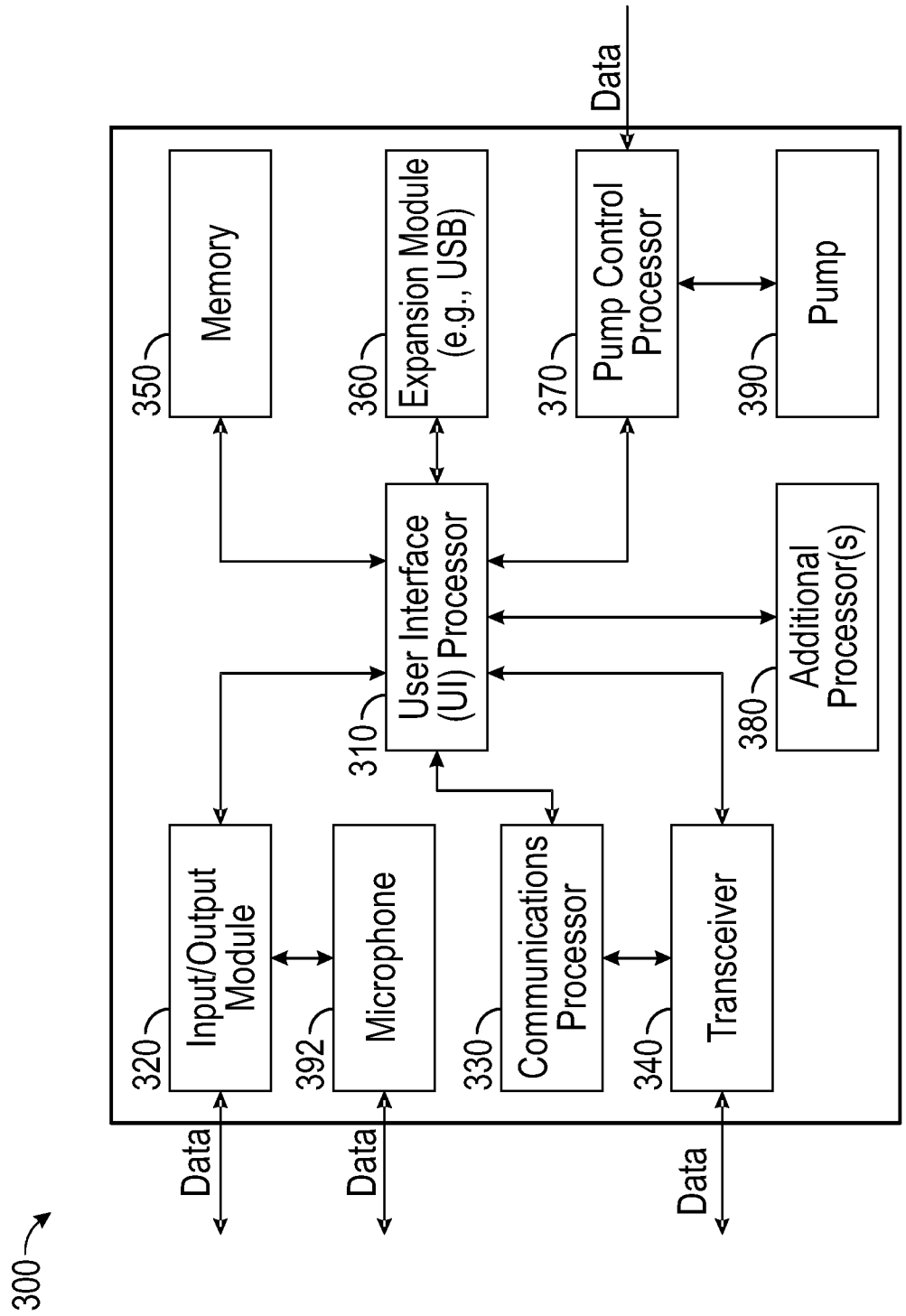
FIG. 3 illustrates a schematic of a reduced pressure wound therapy system.

FIG. 3 illustrates a schematic of a control system 300 which can be employed in any of the embodiments of wound monitoring and/or treatment systems described herein. Electrical components can operate to accept user input, provide output to the user, operate the negative pressure source of a TNP system, provide network connectivity, and so on. It may be advantageous to utilize multiple processors in order to allocate or assign various tasks to different processors. In some cases, a first processor can be responsible for user activity and a second processor can be responsible for controlling another device, such as a pump 390. This way, the activity of controlling the other device, such as the pump 390, which may necessitate a higher level of responsiveness (corresponding to higher risk level), can be offloaded to a dedicated processor and, thereby, will not be interrupted by user interface tasks, which may take longer to complete because of interactions with the user.

Input and output to the other device, such as a pump 390, one or more sensors (for example, one or more pressure sensors configured to monitor pressure in one or more locations of the fluid flow path), or the like, can be controlled by an input/output (I/O) module 320. For example, the I/O module can receive data from one or more sensors through one or more ports, such as serial (for example, I2C), parallel, hybrid ports, and the like. The I/O module 320 can be in communication with the microphone 392. The microphone 392 can be the speaker 232 that includes a microphone or can be configured to operate in microphone mode. In some cases, the I/O module performs one or more filtering, such as a low pass filtering and or a high pass filtering, to process signals received by the microphone 392. In some cases, the filtering can be performed by the processor 310. The filtering can be performed to tune to a particular frequency or set of frequencies. For example, the tuning can be performed to detect one or more signals transmitted by a therapy monitoring device as described herein.

The processor 310 can also receive data from and provide data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, can store data in one or more memory modules 350, which can be internal and/or external to the processor 310. Any suitable type of memory can be used, including volatile and/or non-volatile memory, such as RAM, ROM, magnetic memory, solid-state memory, Magnetoresistive random-access memory (MRAM), and the like.

In some cases, the processor 310 can be a general purpose controller, such as a low-power processor. In other cases, the processor 310 can be an application specific processor. In some cases, the processor 310 can be configured as a "central" processor in the electronic architecture of the system 300, and the processor 310 can coordinate the activity of other processors, such as a pump control processor 370, communications processor 330, and one or more additional processors 380. The processor 310 can run a suitable operating system, such as a Linux, Windows CE, VxWorks, etc.

The pump control processor 370 (if present) can be configured to control the operation of a negative pressure pump 390. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. In some cases, the pump control processor 370 can measure pressure in a fluid flow path, using data received from one or more pressure sensors, calculate the rate of fluid flow, and control the pump. In some cases, the pump control processor 370 controls the pump motor so that a desired level of negative pressure in achieved in the wound cavity 110. The desired level of negative pressure can be pressure set or selected by the user. The pump control processor 370 can control the pump (for example, pump motor) using pulse-width modulation (PWM). A control signal for driving the pump can be a 0-100% duty cycle PWM signal. The pump control processor 370 can perform flow rate calculations and detect alarms. The pump control processor 370 can communicate information to the processor 310. The pump control processor 370 can include internal memory and/or can utilize memory 350. The pump control processor 370 can be a low-power processor.

A communications processor 330 can be configured to provide wired and/or wireless connectivity. The communications processor 330 can utilize one or more antennas or transceivers 340 for sending and receiving data. In some cases, the communications processor 330 can provide one or more of the following types of connections: Global Positioning System (GPS) technology, cellular connectivity (for example, 2G, 3G, LTE, 4G, 5G, or the like), WiFi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software and/or firmware, and the like. In some cases, the communications processor 330 can provide dual GPS/cellular functionality. Cellular functionality can, for example, be 3G functionality. In such cases, if the GPS module is not able to establish satellite connection due to various factors including atmospheric conditions, building or terrain interference, satellite geometry, and so on, the device location can be determined using the 3G network connection, such as by using cell identification, triangulation, forward link timing, and the like. In some cases, the system 300 can include a SIM card, and SIM-based positional information can be obtained. The communications processor 330 can communicate information to the processor 310. The communications processor 330 can include internal memory and/or can utilize memory 350. The communications processor 330 can be a low-power processor.

In some cases, the system 300 can store data illustrated in Table 1. This data can be stored, for example, in memory 350. This data can include patient data collected by one or more sensors. In various cases, different or additional data can be stored by system 300. In some cases, location information can be acquired by GPS or any other suitable method, such as cellular triangulation, cell identification forward link timing, and the like.

TABLE 1

*Example Data Stored*

| Category | Item | Type | Source |
|---|---|---|---|
| GPS | Location | Latitude, Longitude, Altitude | Acquired from GPS |
|  | Timestamp Location Acquired | Timestamp |  |
| Therapy | Total time therapy ON since device activation | Minutes | Calculated on device based on user control |
|  | Total time therapy ON since last maintenance reset | Minutes |  |
|  | Device Placement; accumulated daily hours starting from first Therapy ON after last maintenance reset, stopping at last Therapy OFF before returning for Maintenance and maintenance reset. (Includes both THERAPY ON and THERAPY OFF hours) | Minutes |  |
| Device | Serial Number | Alphanumeric | Set by Pump Utility |
|  | Controller Firmware Version | Alphanumeric | Unique version identifier, hard coded in firmware |
| Events | Device Event Log (See Table 3 for example) | List of Events (See Table 2) | Generated in response to various user actions and detected events |

The system 300 can track and log therapy and other operational data. Such data can be stored, for example, in the memory 350. In some cases, the system 300 can store log data illustrated in Table 2. Table 3 illustrates an example event log. One or more such event logs can be stored by the system 300. As is illustrated, the event log can include time stamps indicating the time of occurrence of a particular event. For example, Table 3 illustrates that the negative pressure source was activated at 1:31:02 UTC on Apr. 22, 2012 to provide therapy at a set point of −120 mmHg (with medium ramp-up intensity) in a continuous mode of operation and that at 1:44:20 UTC on the same day a high flow leak was detected and therapy was stopped at 1:44:24 UTC on the same day. In some cases, additional and/or alternative data can be logged.

TABLE 2

*Example Data Tracked*

| Category | ID | Type | Data Content | Notes |
|---|---|---|---|---|
| Device | 0 | Startup (Created DB) |  | First time, out-of-the-box. |
|  | 1 | Startup (Resumed DB) |  | Subsequent power-ups. |
|  | 2 | Startup (Corrupt DB, Recreated) |  | Corrupt configuration was detected. The database was deleted and recreated, and next run was in out-of-the-box mode. |
|  | 3 | Shutdown (Signaled) |  | Normal shutdown, handed/registered by software. |
|  | 4 | Shutdown (Inferred) |  | Unexpected shutdown; on next power-up, last active time registered as shutdown event. |
| Therapy | 5 | Start Delivery (Continuous) | modes, setpoints | Modes are Y-connect status, and intensity. |
|  | 6 | Start Delivery (Intermittent) | modes, setpoints | Modes are Y-connect status, and intensity. |
|  | 7 | Stop Delivery |  |  |
|  | 8 | Set Therapy Pressure Setpoint | mmHg | This and other therapy adjustment events are only recorded while therapy is being delivered. |
|  | 9 | Set Standby Pressure Setpoint | mmHg |  |
|  | 10 | Set Intermittent Therapy Duration | setting (30 s, 60 s, etc) |  |
|  | 11 | Set Intermittent Standby Duration | setting (30 s, 60 s, etc) |  |
|  | 12 | SetMode | court/intermittent |  |
|  | 13 | Set Intensity | low/med/high |  |
|  | 14 | Set Y Connect | yes/no |  |
| Alarm | 15 | Over Vacuum | high mmHg |  |
|  | 16 | High Vacuum | high deviation mmHg |  |
|  | 17 | Blocked Full Canister | low airflow lpm |  |
|  | 18 | High Flow Leak | high airflow lpm |  |
|  | 19 | Low Vacuum | low mmHg |  |
|  | 20 | Battery Failure |  |  |
|  | 21 | Critical Battery |  |  |
|  | 22 | Low Battery |  |  |
|  | 23 | Inactivity |  |  |
| Maintenance | 24 | Maintenance Reset |  |  |
|  | 25 | Reset to Defaults |  |  |

TABLE 2-continued

Example Data Tracked

| Category | ID | Type | Data Content | Notes |
|---|---|---|---|---|
| | 26 | Software/Device Warning | Warning code | Any detected, minor unexpected software behavior will be logged as an event |
| | 27 | Software/Device Fault | Fault code | Any detected, severe unexpected software behavior will be logged as an event |

TABLE 3

Example Event Log

| Timestamp | Type ID | Type Description | Data |
|---|---|---|---|
| 1:23:45 Apr. 2, 2012 (UTC-12) | 0 | Startup (Created DB) | |
| 1:29:23 Apr. 2, 2012 (UTC-12) | 15 | Set Intensity | medium |
| 1:29:43 Apr. 2, 2012 (UTC-12) | 10 | Set Therapy Pressure Setpoint | 120 mmHg |
| 1:31:02 Apr. 2, 2012 (UTC-12) | 7 | Start Delivery (Continuous) | 120 mmHg continuous, medium intensity, no Y connect |
| 1:44:20 Apr. 2, 2012 (UTC-12) | 20 | High Row Leak | 4 lpm |
| 1:44:24 Apr. 2, 2012 (UTC-12) | 9 | Stop Delivery | |

In some cases, using the connectivity provided by the communications processor 330, the system 300 can upload any of the data stored, maintained, and/or tracked by the system 300 to a remote computing device. In some cases, the following information can be uploaded to the remote computing device: activity log(s), which includes therapy delivery information, such as therapy duration, alarm log(s), which includes alarm type and time of occurrence; error log, which includes internal error information, transmission errors, and the like; therapy duration information, which can be computed hourly, daily, and the like; total therapy time, which includes therapy duration from first applying a particular therapy program or programs; lifetime therapy information; device information, such as the serial number, software version, battery level, etc.; device location information; patient information; and so on. The system 300 can also download various operational data, such as therapy selection and parameters, firmware and software patches and upgrades, and the like. The system 300 can provide Internet browsing functionality using one or more browser programs, mail programs, application software (for example, apps), etc. Additional processors 380, such as processor for controlling one or more user interfaces (such as, one or more displays), can be utilized. In some cases, any of the illustrated and/or described components of the system 300 can be omitted depending on an embodiment of a wound monitoring and/or treatment system in which the system 300 is used.

Any of the negative pressure wound therapy devices described herein can include one or more features disclosed in U.S. Pat. No. 9,737,649 or U.S. Patent Publication No. 2017/0216501, each of which is incorporated by reference in its entirety.

Monitoring Delivery of Therapy

A wound therapy system, such as the negative pressure wound therapy system 100, can include one or more devices configured to monitor delivery of therapy (sometimes referred to as a therapy monitoring device). A therapy monitoring device can be positioned in fluid flow path or at the wound, such as under the wound dressing or in another location in the fluid flow path. The therapy monitoring device can monitor one or more characteristics associated with delivery of the therapy and provide an indication (or a signal) in response to detecting that the one or more characteristics are being met or are not being met. The indication can be communicated to a therapy device, such as a negative pressure wound therapy device. The therapy monitoring device can provide the indication in response to determining that a particular threshold has (or has not been) satisfied. Otherwise, the therapy monitoring device can operate in a low power state, as described herein.

For example, the therapy monitoring device can monitor negative pressure levels at the wound and provide an indication that a negative pressure level satisfies (such as, meets of falls below) a minimum threshold negative pressure level (which can indicate that the negative pressure level at the wound is not sufficient), satisfies (such as, meets or exceeds) the threshold overpressure level (which can indicate that the negative pressure at the wound is too high), or the like. As another example, the therapy monitoring device can monitor negative pressure levels over time and provide an indication that a duration of negative pressure wound therapy satisfies (such as, meets of falls below) a threshold therapy duration (for example, 22 hours in a 24-hour period). The monitoring device can be configured to monitor the negative pressure levels at the wound and track a cumulative amount of time during which the negative pressure level at the wound satisfies (for example, meets of falls below) the minimum threshold negative pressure level. The monitoring device can be configured to provide the indication in response to determining that the cumulative amount of time satisfies a threshold associated with the threshold therapy duration. For example, the indication can be provided in response to determining that the cumulative amount of time meets or exceeds 2 hours (or less or more) in a 24-hour period (or less or more). This can indicate non-compliance with the duration of negative pressure wound therapy.

As another example, the therapy monitoring device can monitor flow in the fluid flow path and provide an indication that the flow satisfies a threshold level indicating a leak. Satisfying such threshold can be indicative of the wound becoming or being too dry. As another example, therapy additional to or alternative to negative pressure can be provided, such as oxygen therapy, nitrogen therapy, or the like. The therapy monitoring device can monitor a level of, for instance, oxygen, nitrogen, or the like at the wound and provide an indication that the level satisfies a threshold level (which can indicate that the level at the wound is too low), satisfies a maximum level (which can indicate that the level to the wound is too high), or the like. The therapy monitoring device can monitor concentration of, for instance, oxygen, nitrogen, or the like at the wound.

Use of a therapy monitoring device can ensure safe delivery of therapy, such as negative pressure wound therapy. For example, detecting and communicating pressure at the wound can promote safety, prevent wound maceration, promote prolonged application of wound therapy, assist with determining compliance with wound therapy regime or prescription, or the like.

Although certain portions of the disclosure refer to monitoring or detecting pressure levels, for example with one or more pressure sensors, the approaches described in such portions are not limited to monitoring and detection of pressure. The approaches described in such portions of the disclosure can be used to monitor any of the characteristics associated with delivery of the therapy, as described herein.

A therapy monitoring device can be configured to detect pressure levels at a wound and communicate information to the negative pressure wound therapy device, such as to a controller of the device (for example, the controller 310). The therapy monitoring device can detect when the pressure at a wound satisfies (such as, meets or falls below) the minimum threshold negative pressure level. The minimum threshold negative pressure level can be indicative of a minimum acceptable negative pressure therapy level, which can indicate loss of negative pressure at the wound. An instantaneous loss can be detected, a loss for a period of time can be detected (such as, pressure satisfies the threshold negative pressure level for a duration of time), or the like. Additionally or alternatively, the therapy monitoring device can monitor the duration of negative pressure wound therapy, as described herein. This can help to ensure that negative pressure wound therapy is being applied to the wound at least at a minimum (or baseline) therapeutic level, which can, among other things, promote wound healing and prevent wound maceration. The therapy monitoring device can detect overpressure at a wound based on detecting that the pressure satisfies (such as, meets or exceeds) the threshold overpressure level. The threshold overpressure level can be indicative of a negative pressure safety level.

The therapy monitoring device can include a pressure sensor configured to detect pressure changes at the wound, such as, under the wound dressing, or in another location in the fluid flow path. The pressure sensor can be one or more of a capacitive sensor, a strain gauge, a piezoelectric sensor, an optical sensor, a mechanical sensor, or the like. The pressure sensor can be configured to provide absolute or differential pressure measurements. The pressure sensor can be configured to generate a signal (such as, an electrical signal) when the sensor detects a threshold level of pressure and/or when the level of pressure is outside an operational range. Operational range can be defined as a pressure range of, for example, about ±1 mmHg or less, about ±5 mmHg, about ±10 mmHg, about ±20 mmHg or more, around a pressure set point. The pressure set point can be, for example, about −50 mmHg or less, −60 mmHg or less, −70 mmHg, −80 mmHg, −90 mmHg or more. In some cases, the pressure sensor can be configured to transmit (or be connected to a transmitter configured to transmit) the signal generated by the pressure sensor. The transmitter can include a transceiver.

The pressure sensor can include a pressure switch. For example, a diaphragm pressure switch, piston pressure switch, capsule pressure switch, bellow pressure switch, Bourdon tube pressure switch, electrical pressure switch, and/or the like can be used. The pressure switch can provide an indication when pressure satisfies a threshold.

The pressure sensor can be configured to operate in two or more states. For example, the pressure sensor can be configured to operate in three states for when the pressure is at or within an operational range, as described herein, when the pressure is below the operational range, and when the pressure is above the operational range.

The pressure sensor can comprise or be positioned in an elastic or flexible enclosure that compresses in response to application of pressure. The compression of the enclosure caused by application of pressure can cause movement or deflection of a sensing element, such as a diaphragm, which can be connected to a strain gauge. Deflection of the diaphragm can cause deformation of the strain gauge. This can cause resistance of the strain gauge to change responsive to the applied pressure. An electrical circuit can be used to detect the one or more states of the pressure sensor (for example, based on the resistance of the strain gauge).

The therapy monitoring device can be at least partly positioned in an elastic or flexible enclosure within which positive pressure is maintained. The enclosure can be filled with gas. For example, the enclosure can be a balloon within which a volume of gas is sealed. The enclosure can be positioned in the fluid flow path (such as, in the wound) using any of the approaches described herein. Application of negative pressure by the negative pressure wound therapy device can cause the pressure within the enclosure to be increased (or become more positive). Increase of positive pressure within the enclosure can cause the enclosure to be expanded. A pressure sensor of the therapy monitoring device (for example, an absolute pressure sensor) can sense the increase in positive pressure resulting from the application of negative pressure. The pressure sensor can be configured to generate a signal (such as, an electrical signal) when the sensor detects a level of positive pressure corresponding to the threshold level of negative pressure and/or when the level of positive pressure is outside an operational range corresponding to the negative pressure operational range. Advantageously, use of the enclosure can isolate one or more electronic components of the therapy monitoring device (including, for instance, the power source) from the wound, provide protection from fluid ingress, or the like.

The therapy monitoring device can include multiple pressure sensors (or any other additional or alternative sensors described herein). Additionally or alternatively, multiple therapy monitoring devices can be used. Among other advantages, this can provide redundancy, provide the ability to monitor application of therapy in multiple locations, or the like.

A transmitter, such as an oscillator, can be in communication with the pressure sensor (and/or any of the other sensors described herein, such as an oxygen sensor, a moisture sensor, or the like). The transmitter can generate an acoustic signal or electromagnetic radiation (such as, microwave, RF, light, or the like) in response to pressure detected by the pressure sensor. The transmitter can transmit an encoded signal. For example, the transmitter can transmit a modulated signal, such as pulse width modulated signal. The signal can be transmitted at a particular frequency, such as a frequency outside the range of human hearing. For example, the transmitted signal can be higher than the upper limit of human hearing (such as, about 20 kHz). The transmitted signal can be at a different (such as, higher) frequency than that frequencies generated by electronic devices, such as a negative wound therapy apparatus This can help with isolating the transmitted signal from ambient noise and/or noise associated with the operation of the apparatus and can facilitate detection of the transmitted signal. The signal can be transmitted through one or more conduits or lumens connecting the wound dressing and the negative wound therapy device. For example, an acoustic signal can be transmitted through a conduit connecting the wound dressing to the device, which can facilitate more reliable transmission of the signal.

The transmitter can, in some cases, be configured to transmit light. For example, the transmitter can include a light source (for example, an LED). The light source can be connected to a light pipe (such as, one or more conduits or lumens) to facilitate transmission of the light signal to a negative pressure therapy apparatus or another device.

In some cases, the signal can be transmitted at the frequency of 2 Hz or less, 4 Hz, 8 Hz, 16 Hz, 100 Hz, 1 kHz, or 10 kHz or more, or the like. The therapy monitoring device can be configured to provide regular pressure readings by generating signals at various time intervals, such as 30 minutes or less, 1 hour, 2 hours, 4 hours or more, or the like. In some cases, the signal can be generated and transmitted when pressure outside the operational range and/or satisfying a threshold is detected. Such operation can facilitate conserving capacity of a power source of the therapy monitoring device and prolong its operational life. One or more of the therapy monitoring device or electronic control circuitry can operate in a first power state or mode during which it consumes very little power. The first state can be the low power state or mode. Periodically or in response to satisfying a condition as described herein, one or more of the therapy monitoring device or control circuitry can transition to a second power state or mode in which it measures pressure. If measured pressure is determined to satisfy a threshold and/or be outside the operational range, one or more of the therapy monitoring device or control circuitry can transmit (or cause a transmitter to transmit) the signal. One or more of the therapy monitoring device or control circuitry can return to the first power state after transmitting (or causing transmission of) the signal.

The therapy monitoring device can include or be connected to control circuitry. The control circuitry can include one or more controllers or processors. The control circuitry can be configured to operate at least one of the wound pressure sensor and the transmitter. For example, the control circuitry can be configured to operate the transmitter to modulate the signal (such as, using pulse width modulation). As another example, the control circuitry can operate the wound pressure sensor to measure pressure at the wound (such as, periodically).

The therapy monitoring device can include or be connected to a valve, such as a solenoid valve. In some cases, when overpressure is detected, the valve can be opened to allow gas (such as, air) into the flow path to reduce the level of negative pressure at the wound. The valve can be operated by the control circuitry.

The therapy monitoring device (and/or the negative pressure wound therapy device, as described herein) can generate an indication, which can be an alarm. The alarm can be one or more of a visual, acoustic, tactile, or the like. The indication can be generated, for example, in accordance with the IEC 60601-1 standard for medical devices or similar standard. For example, the indication can be associated with one or more dynamic alarms having different priorities in accordance with the IEC 60601-1 standard.

One or more of the therapy monitoring device, transmitter, or control circuitry can be powered by a power source. The power source can include one or more batteries. The power source can include one or more capacitors. The power source can include an electroactive polymer (such as, piezoelectric material) configured to generate electric charge responsive to one or more of compression or decompression due to application of negative pressure and loss of negative pressure, as described herein.

The therapy monitoring device can include one or more mechanical capacitors. A mechanical capacitor can include two plates separated by dielectric material, such as elastic or compressible dielectric material. The mechanical capacitor can be compressed by application of vacuum at the wound. The mechanical capacitor can be decompressed, for example, at the minimum threshold negative pressure level and/or at a pressure level outside the operating range of negative pressure wound therapy. Changes in the capacitance caused by the compression and subsequent decompression (resulting from loss of negative pressure) of the mechanical capacitor can be detected by the control circuitry. In response to the detection, the control circuitry can generate and transmit the signal.

In some cases, one or more of the therapy monitoring device or the control circuitry can be inactive (such as, operate in a low power mode or state) until detection of the minimum threshold negative pressure level, a pressure level outside the operating range of negative pressure wound therapy, and/or any other characteristic associated with delivery of the therapy described herein. As described herein, one or more of the therapy monitoring device or control circuitry can be powered on by application of a negative pressure that satisfies the threshold and/or is outside the operating range. In some cases, the therapy monitoring device can comprise or be connected to a diaphragm switch. Upon application of negative pressure that satisfies the threshold and/or is outside the operating range, the diaphragm switch can operate a latching circuit (which can be connected to or part of the control circuitry) to power one or more of the control circuitry or the therapy monitoring device. The latching circuit can include one or more switches, such as transistors, logic gates (such as, latches), or the like. The power source can be isolated from one or more of the therapy monitoring device or control circuitry.

The therapy monitoring device can be activated to monitor one or more characteristics associated with delivery of the therapy. Activation can, for example, cause power to be provided to the control circuitry. For instance, activation can activate a latching circuit. As another example, activation can cause the control circuitry to transition from a deep sleep state to the low power state. The therapy monitoring device can be activated in response to a user pressing a button, switch, or the like (which can be positioned on an external surface of the housing). The therapy monitoring device can include one or more sensors configured to detect positioning of the therapy monitoring device in a wound of a patient or in a fluid flow path. Such one or more sensors can include one or more of touch sensors (for example, capacitive, resistive, etc. touch sensors), temperature sensors, moisture sensors, optical sensors, acoustic sensors, or the like. The therapy monitoring device can be activated in response to the one or more sensors detecting a condition indicative of the therapy monitoring device being in use. For instance, a touch sensor can detect contact with the patient. As another example, a temperature sensor can detect body temperature (such as, 36.5 to 37.5 Celsius). As yet another example, the therapy monitoring device can be activated in response to detection of application of negative pressure wound therapy, using any of the approaches described herein.

In some cases, the therapy monitoring device can include a resonator. The resonator can be positioned in the fluid flow path. The resonator can be a mechanical resonator. The resonator can be configured to oscillate at one or more frequencies (which can be referred to as resonant frequencies). The one or more frequencies can correspond to or be associated with the intensity of the negative pressure flowing through the fluid flow path.

The one or more frequencies generated by the resonator can be detected by the therapy monitoring device and can be processed to detect one or more negative pressure levels. For example, the detection can be performed acoustically, such as with one or more microphones, by measuring the reflection of the acoustic waves, such as with a radar, or the like. As another example, the detection can be performed electromechanically, such as with a ceramic cartridge (which can include piezoelectric material), magnetic cartridge (which can include a moving magnet, moving coil, or the like). Such cartridge can be similar to the ones used in phonographs for recording and reproduction of sound. As yet another example, the detection can be performed optically, such as based on the detection of vibrations of one or more fibers due to the oscillations. As yet another example, the detection can be performed using a Hall effect sensor, which can be configured to detect the magnetic field generated by a magnetic component that moves due to the oscillations.

The resonator can be positioned in a conduit connecting the wound dressing to the negative pressure source, such as the conduit 140. The resonator can be positioned in a conduit connected to the external environment (sometimes referred to as an air leak or bleed), one or one or more branches of a flow connector (which can be a flow separator or amalgamator), or the like. The flow connector can be a multi-branch connector. The resonator can include one or more hydrophobic portions or barriers at one or more of its ends. The resonator can be positioned in a bypass with the one or more hydrophobic barriers, which can facilitate maintaining the one or more frequencies of the resonator.

All or some of the components comprising the therapy monitoring device can be supported by (such as, enclosed by) a housing. This can ensure that the electrical components do not come into contact with fluid aspirated from the wound or provided to the wound. The housing can be made of a hydrophobic material, such as polyurethane, polyvinyl chloride (PVC), nylon, polyethylene, silicone, or the like. The housing can be made of flexible or substantially flexible material. In some cases, one or more components of the therapy monitoring device may be at least partially exposed. For example, a resonator can be positioned in the fluid flow path as described herein.

One or more components of the therapy monitoring device can be placed on a flexible or substantially flexible substrate, such as a circuit board. The substrate can additionally or alternatively be extensible or substantially extensible. For example, the substrate can include flexible or substantially flexible film. One or more electrical components and connections can be printed on or positioned on the film. For example, one or more electrical connections can be printed using conductive ink. The substrate can be positioned over a hole or opening in the cover (such as, the drape 120), positioned under the cover, or the like.

In addition to or alternatively to one or more pressure sensors or any other sensors disclosed herein, the therapy monitoring device can include a moisture sensor configured to monitor moisture levels at the wound (or in the dressing or fluid flow path). The therapy monitoring device can provide an indication in response to determining that the detected moisture level satisfies (such as, meets or exceeds) a moisture threshold indicative of maximum amount of fluid pooled in the wound. Satisfying the moisture threshold can be indicative of excessive pooling of fluid in the wound caused by the negative pressure at the wound falling below the minimum acceptable level. The moisture sensor can include at least one pair of electrodes configured to determine impedance (or capacitance) across the electrodes. Dryer environments can be associated with to higher impedance and moister environments can be associated with lower impedance.

In addition to or alternatively to one or more pressure sensors or any other sensors disclosed herein, the therapy monitoring device can include an oxygen sensor that measures the concentration of oxygen at the wound (or in the dressing or fluid flow path). Oxygen concentration can correspond to the partial pressure of oxygen. The therapy monitoring device can provide an indication in response to determining that the level of oxygen satisfies (such as, meets or exceeds) an oxygen pressure threshold, which can be associated with the minimum acceptable level of negative pressure. Because the partial pressure of oxygen is reduced with higher levels of negative pressure, satisfying the oxygen pressure threshold can be indicative of the negative pressure at the wound falling below the minimum acceptable level. The oxygen sensor can be an optical sensor, a lambda probe, Clark-type sensor, or the like.

Figure 4:
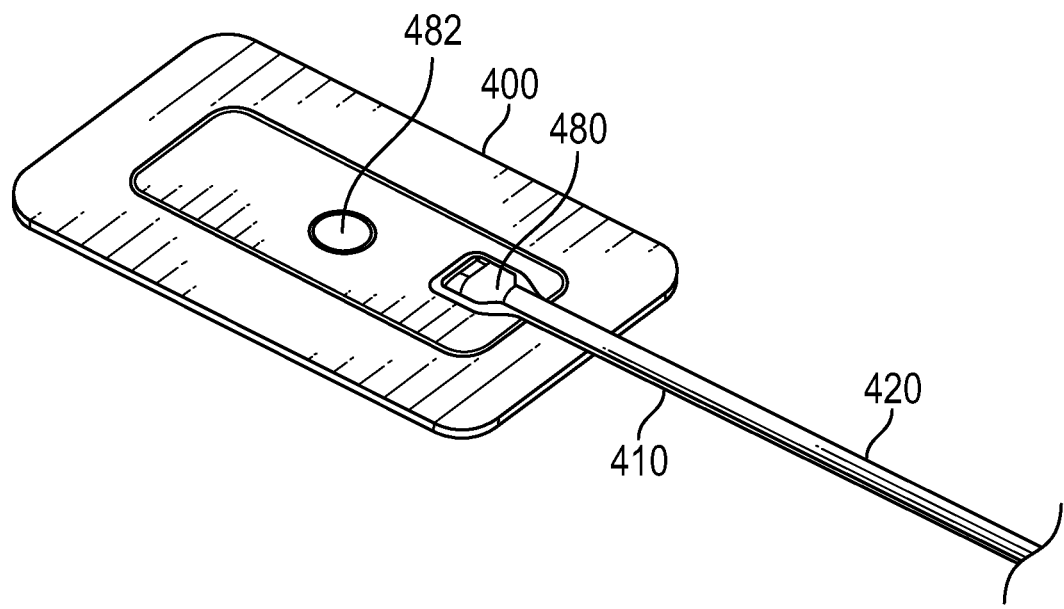
FIG. 4 illustrates a therapy monitoring device disposed on a dressing.

FIG. 4 illustrates a therapy monitoring device 482 disposed on or in a dressing 400. The therapy monitoring device 482 can include one or more features of any therapy monitoring devices disclosed herein (and vice versa). A fluidic connector 410 (sometimes referred to as adaptor) can connect the dressing 400 to a negative pressure source. The fluidic connector 410 can include an elongate conduit, or a bridge 420 having an applicator 480 at the distal end. The applicator 480 can be configured to be positioned on the dressing 400. For example, the applicator 480 can include adhesive for attaching the applicator 480 on the dressing. The proximal end of the connector 410 can be connected to a negative pressure wound source, such as the pump 150. In some cases, the fluidic connector 410 can be connected to a connector tube or lumen that connects to the negative pressure source. The fluidic connector 410 can be one or more of, flexible, soft, conformable, or the like. In some cases, the fluidic connector 410 can be a Renasys Soft Port connector available from Smith & Nephew. In some cases, the pump may be attached or mounted onto or adjacent the dressing 400. In some cases, the dressing 400 may be connected to two or more fluidic connectors 410.

The wound dressing can include a cover. The cover layer can be the upper most layer of the dressing. In some cases, the wound dressing can include a second cover for positioning over the layers of the wound dressing and any of the integrated components. The second cover can be the upper most layer of the dressing or can be a separate envelope that encloses the integrated components of the topical negative pressure system.

As depicted in FIG. 4, the therapy monitoring device 482 can be disposed in or on the dressing 400. The therapy monitoring device 482 can be disposed in or on the dressing 400 such that the device 482 is in fluidic communication with the wound. In some cases, the therapy monitoring device 482 can be disposed in the dressing 400 such that the therapy monitoring device 482 is under the upper most layer of the dressing, such as the cover. In some cases, the therapy monitoring device 482 can be positioned near or on the applicator 480.

The therapy monitoring device 482 can be positioned in the fluidic connector 410. For example, the therapy monitoring device 482 can be molded into a wall of the fluidic connector 410, inserted into a pocket on the fluidic connector 410, or the like. In some cases, the therapy monitoring device 482 can be attached to a branch connection in the fluidic connector 410, such as a T-connection.

Figure 5A:
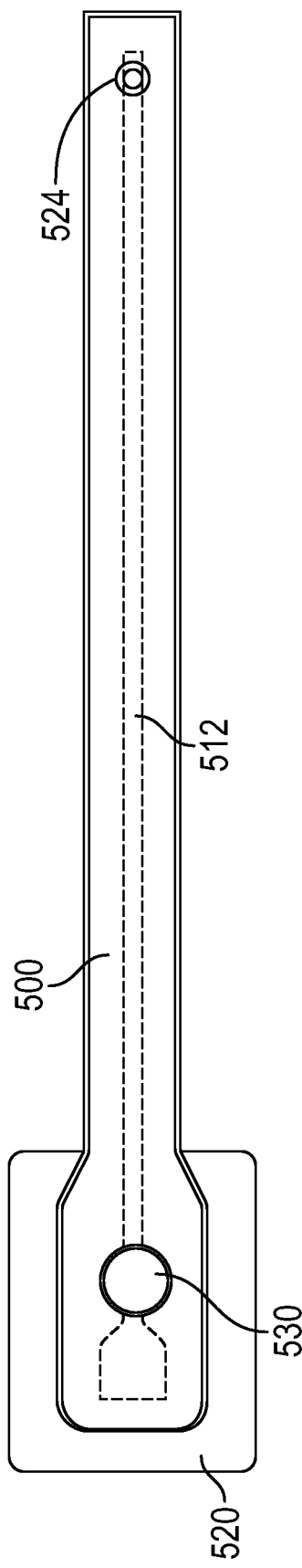
FIGS. 5A-5B illustrate a therapy monitoring device disposed on a fluidic connector.
Figure 5B:
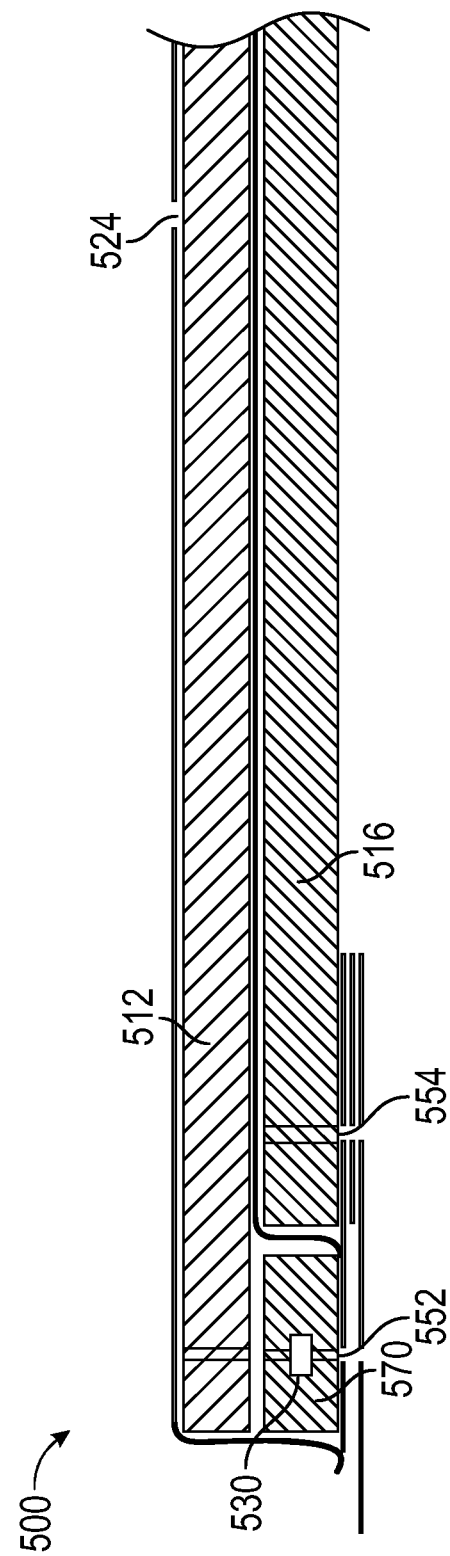

FIGS. 5A-5B illustrate a therapy monitoring device 530 disposed on a fluidic connector 500 (sometimes referred to as adaptor). The therapy monitoring device 530 can include one or more features of any therapy monitoring devices disclosed herein (and vice versa). The fluidic connector can be same or similar to the fluidic connector 410 (and vice versa). The fluidic connector 500 can include an air leak 524, which can provide a controlled (or reference) flow of gas from the external environment (such as, air from the atmosphere). Controlled flow of gas from the external environment can facilitate removal of exudate and/or solid material from the wound. The fluidic connector 500 can include a bridge having a proximal end and a distal end. The distal end can include an applicator 520. The applicator 520 can be connected to a wound dressing 400. The applicator 520 may comprise an attachment point for the bridge portion at the distal end, for example. using a section of double-sided adhesive tape. Different attachment mechanisms can be additionally or alternatively used (for example, heat sealing, welding, or adhesives). The bridge can include an upper channel 512 and a lower channel 516. The air leak 524 can include an opening or channel extending through an upper layer. The air leak 524 can be in fluidic communication with the upper channel 512. The air leak 524 can include a filter configured to prevent release of one or more of odors or bacteria into the surrounding environment, prevent one or more bacteria, debris, or other material from the external environment from entering the fluid flow path, limit the flow of gas from the external environment, or the like. The lower channel 512 can be in fluidic communication with the negative pressure source, such as the pump 150. Wound exudate can be aspirated though the lower channel 512. Wound exudate can be stored in a canister, such as the canister 220.

As shown in FIG. 5B, the suction adaptor may include two fluid flow paths or channels, an upper channel 512 and a lower channel 516. The distal ends of with the channels can include at least one through aperture, such as the apertures 552, 554. The at least one aperture can be used for applying negative pressure to the wound and aspirating wound exudate. A spacer 570 can be positioned under the distal end of the upper channel 512 and extend distally beyond the distal end of the lower channel 516. The spacer 570 can supports the distal end of the upper channel 512. One or more of the spacer 570, the upper channel 512 or the lower channel 516 can be constructed from any material suitable for transmitting fluid. Such materials can include, for example, open-celled foams (such as, polyethylene or polyurethane), fabrics (such as, knitted or woven spacer fabrics, including one or more of knitted polyester 3D fabrics, Baltex 7970® or Gehring 879® or a nonwoven materials), or the like.

As shown in FIG. 5B, the suction adapter 500 can include two apertures: an air leak aperture 552 and a suction aperture 554. Both apertures can be formed at the distal end of the fluidic connector 500. The air leak aperture 552 and/or the suction aperture 554 can include a plurality of apertures. As illustrated, the apertures 552 and 554 may be spaced apart, with the aperture 554 located distally of the aperture 552. The applicator 520 may have two openings configured to be aligned with the air leak aperture 552 and the suction aperture 554. As shown in FIG. 5B, the air leak aperture 552 may be fluidically connected to the upper channel 512, thereby forming an air leak flow extending from the air leak 524 to the air leak channel aperture 552. As shown in FIG. 5B, this air leak flow can extend through the spacer 570. The suction aperture 554 may be fluidically connected to the lower channel 516, thereby forming a suction flow extending from the connector and/or the source of negative pressure. In some cases, the upper channel 512 may be fluidically separate from the lower channel 516.

The air leak aperture 552 and the suction aperture 554 may be sufficiently spaced apart from each other, such that wound exudate aspirated through the suction aperture 554 does not enter the air leak aperture 552. The upper channel 512 may include a filter (not shown) adjacent the air leak aperture 552 configured to prevent entering of the wound exudate into the upper channel 512 and blocking the upper channel 512. The filter may be permeable to gas to allow the gas from the external environment to be circulated under the wound dressing, but may be impermeable to liquid and/or bacteria. The lower channel 516 may include a filter (not shown) adjacent the suction aperture 554. The filter may be configured to substantially prevent wound exudate from entering the lower channel 516. The filter may be impermeable to liquids, but permeable to gases. The filter can act as a liquid barrier to ensure that liquids are not able to escape from the wound dressing, which can be absorbent. In such cases, a canister to collect the wound fluid may not be used. The filter may be hydrophobic. The filter can be attached or sealed to the adapter and/or the cover of the wound dressing. For example, the filter may be molded into the adapter 500, or may be adhered to the lower layer of the adapter 500 using an adhesive such as, but not limited to, a UV cured adhesive.

As depicted in FIG. 5A, the therapy monitoring device 530 can be disposed or positioned in or on the distal end of the adapter 500. The therapy monitoring device 530 can be in fluidic connection with the upper channel 512. The therapy monitoring device 530 can detect negative pressure at the wound or negative pressure being delivered to the wound. In some cases, the therapy monitoring device 530 can disposed within the adapter 500 and positioned under the upper layer of the adapter such that the therapy monitoring device 530 is not exposed (or at least partially not exposed) to the external environment. In some cases, the therapy monitoring device 530 can be positioned on the surface of the adapter 500 can be exposed to the external environment.

The therapy monitoring device 530 may be positioned in fluidic communication with the upper channel 512. For example, as illustrated in FIG. 5B, the therapy monitoring device 530 can be positioned near the air leak aperture 552. Such positioning can allow the therapy monitoring device 530 to detect negative pressure at the wound. In some cases, the therapy monitoring device 530 can be placed near the suction aperture 554 and/or otherwise in fluidic communication with the lower channel 516.

As described herein, the therapy monitoring device 530 can include a resonator. The resonator may be positioned in fluidic communication with in the upper channel 512 or the lower channel 516. For example, the resonator can be positioned as illustrated in FIG. 5B.

In some cases, the adapter 500 can have fluidically separate or isolated air leak flow path (the upper channel 512) and suction flow path (the lower channel 516). Other arrangements for the adapter 500 having fluidically separate air leak and suction flow paths are possible. For example, the air leak flow patch and the suction flow path may be disposed side-by-side, instead of one channel being placed on top of the other. Two physically separated adapters 500 may be provided with one configured to provide aspiration and the other configured to provide the reference flow.

Any of the fluidic connectors disclosed herein can include one or more features disclosed in U.S. Pat. Nos. 8,801,685 and 9,050,398 and International Patent Application No. PCT/EP2019/068201, filed on Jul. 8, 2019, each of which is incorporated by reference in its entirety.

Therapy Monitoring

Figure 6:
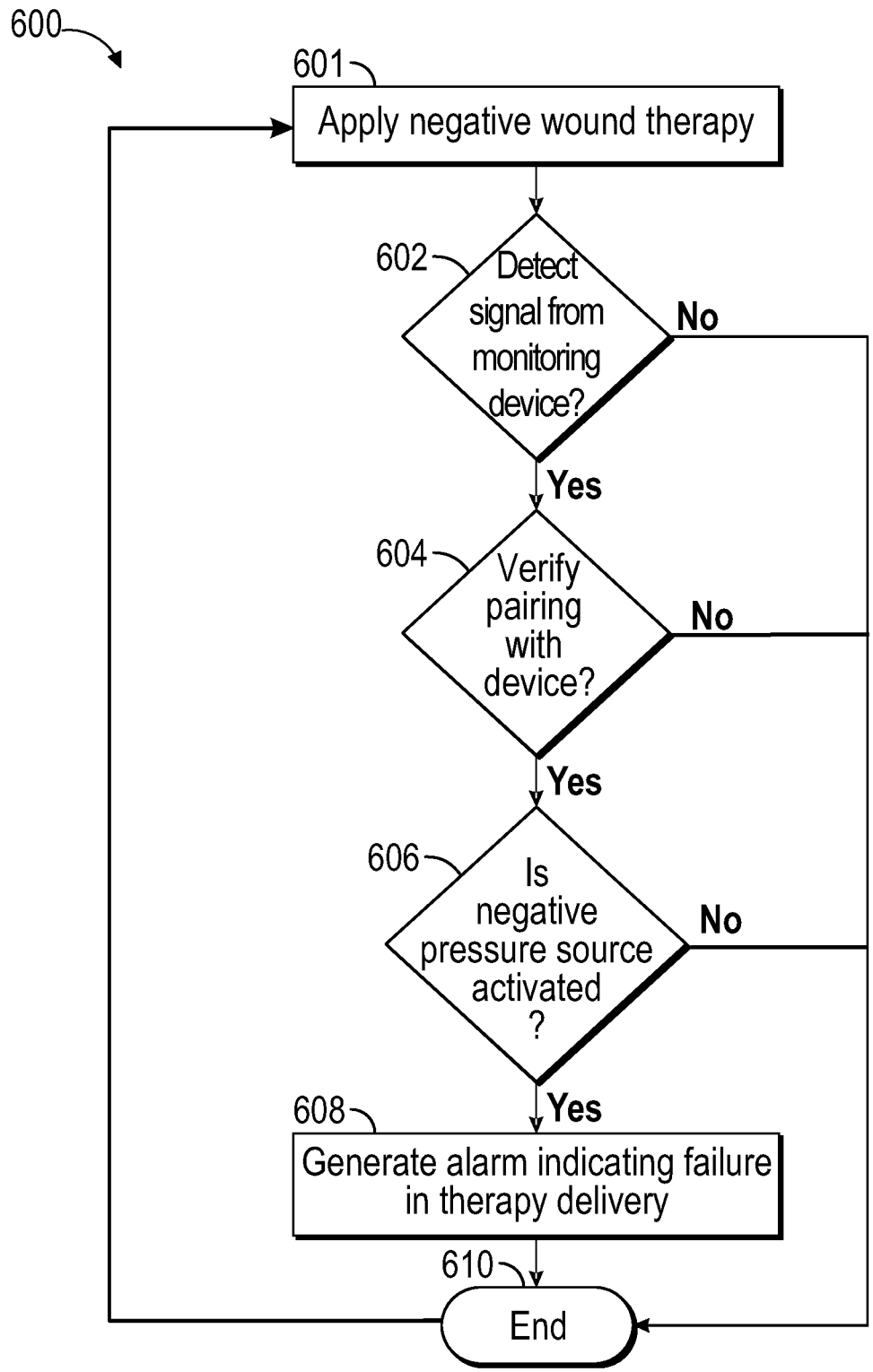
FIG. 6 illustrates a process of monitoring and/or detection.

FIG. 6 illustrates a monitoring and/or detection process. The process 600 can be performed by a negative pressure wound therapy system (such as, the system 100) that includes one or more therapy monitoring devices (which can include one or more features disclosed herein). For example, the process 600 can be implemented by at least one processor of the system, such as the processor 310 alone or in combination with the processor 330. The process can generate an alarm in response to, for instance, detection of application of negative pressure that satisfies the threshold and/or is outside the operating range, as described herein. The process 600 can be extended to the monitoring any negative pressure therapy parameter and/or any parameter of another therapy, as described herein.

The process can start in block 601 where the negative pressure wound therapy apparatus applies negative wound therapy. In some cases, a therapy prescription specifies a threshold level of pressure, duration of application of negative pressure, and/or an operational range. For example, the threshold level of pressure can correspond to the minimum acceptable level of negative pressure. In some cases, the therapy prescription specifies time intervals in which the threshold level of pressure is applied. In block 602, the process 600 can determine whether an indication from the therapy monitoring device is detected. As described herein, the indication can be transmitted in response to detection of application of negative pressure that satisfies the threshold and/or is outside the operating range. The indication can include a sound or electromagnetic radiation emitted by the therapy monitoring device. The therapy monitoring device may generate the indication in response to detecting that the pressure at the wound falls below the minimum acceptable level. The therapy monitoring device can generate the indication in response to the pressure at the wound exceeding a threshold overpressure level.

The negative pressure wound therapy apparatus can detect the indication via a detector. For example, the detector can include a microphone for detecting acoustic signals. As another example, the detector can include an RF receiver for one or more of detecting or transmitting electromagnetic radiation (such as, a transceiver). As yet another example, the detector can include an optical detector (such as, a photodetector) for detecting light. In some cases, an indication signal can travel through a connector providing a fluidic connection between the wound and the negative pressure wound therapy apparatus.

In some cases, the indication can be additionally or alternatively detected by a computing device, such as a computer (for example, clinician's computer), server, mobile computing device, pager, monitoring unit hospital monitoring system, or the like. The therapy monitoring device can transmit the indication via one or more of Near Field Communication (NFC), Bluetooth, Zigbee, Wi-Fi, or the like. The computing device can generate the alarm as described herein. Although certain portions of the disclosure refer to detection of one or more indications transmitted by the therapy monitoring device(s) by a negative pressure wound therapy apparatus, the approaches described in such portions can be applied to detection by any computing device, as described herein.

If in block 602 the process 600 detects the indication from the therapy monitoring device, the process can transition to block 604. Otherwise, the process can transition to block 610. In block 604, the process can verify that the therapy monitoring device has been paired with the negative pressure wound therapy system (or device) using any of the approaches disclosed herein. Verification in block 604 can ensure that the negative pressure wound therapy system is communicating with the correct therapy monitoring device, such as the device monitoring the wound dressing fluidically connected to a negative pressure source of the system.

If in block 604 the process 600 determines that the therapy monitoring device has been paired with the negative pressure wound therapy device, the process can transition to block 606. Otherwise, the process can transition to block 610. Block 604 can be optional.

In block 606, the process 600 can determine whether the negative pressure source is activated. This determination can involve verifying that the negative pressure source is providing or supplying negative pressure to the wound. If the process determines that the negative pressure source is not activated, the process can transition to block 610. For example, the process can determine that the negative pressure source is inactive because the therapy has ended or there is a pause in therapy delivery. In such cases, the indication detected by the negative pressure wound therapy apparatus can indicate a false detection. If the process determines that the negative pressure source is activated, then the process can transition to block 608.

In block 608, the process 600 can generate the alarm. For example, the negative pressure wound therapy apparatus can generate the alarm. The failure indicated by the alarm can depend on one or more of the configuration of the therapy monitoring device and the therapy delivery prescription. For example, the therapy monitoring device can be configured to provide the indication in response to detecting that the pressure at the wound falls below the minimum acceptable level. In such case, in block 608, the alarm can indicate one or more leaks in the fluid flow path. The negative pressure wound therapy apparatus can be configured to increase applied pressure in conjunction with or in place of generating the alarm. As another example, the therapy monitoring device can provide the indication in response to the pressure at the wound exceeding a threshold overpressure level. In such case, the alarm can indicate that there is overpressure in the fluid flow path (such as, due to one or more blockages). The negative pressure wound therapy apparatus can be configured to reduce the level of supplies pressure or terminate supply of pressure in conjunction with or in place of generating the alarm.

In some cases, intermittent or cyclical negative pressure wound therapy can be applied. Applied negative pressure can be switched between at least one low level and at least one high level. Low level can correspond to higher absolute pressure (or more positive pressure) than that at the high level. The therapy monitoring device can be configured to provide the indication in response to detecting pressure at the wound that satisfies (such as, meets or falls below) the low level of negative pressure. Such configuration can confirm that the therapy monitoring device is operating properly when cyclical therapy is applied. The therapy monitoring device providing the indication at a time different from the time when the low level of negative pressure is being applied by the negative pressure source, can be indicative of loss of negative pressure at the wound.

The therapy monitoring device can additionally or alternatively be configured to generate the same or different indication in response to satisfying (such as, meeting) the high level of negative pressure. Such configuration can confirm that the therapy monitoring device is operating properly when cyclical therapy is applied. The therapy monitoring device generating the indication at a time different from the time when the high level of negative pressure is being applied by the negative pressure source, can be indicative of overpressure in the fluid flow path.

Additionally or alternatively, the therapy monitoring device can be configured to generate staged indications at different pressure levels. For example, the therapy monitoring device can be configured to generate a first indication in response to detecting pressure at the wound that satisfies (such as, meets or falls below) the low level of negative pressure. The therapy monitoring device can be configured to generate a second indication in response to detecting pressure at the wound that satisfies (such as, meets or falls below) a negative pressure level that is lower (such as, more positive) than the low level of negative pressure. The low level can be, for example, −70 mmHg, and the negative pressure level lower than the low level can be, for example, −35 mmHg. The first indication can indicate partial or substantially partial loss of pressure. The second indication, which can be different from the first indication, can indicate complete or substantially complete loss of pressure. The therapy monitoring device can be configured to generate a third indication in response to detecting pressure at the wound that satisfies (such as, meets or exceeds below) a negative level that is higher (such as, more negative) than the low level of negative pressure. Such level can be, for example, −90 mmHg. The third indication can indicate normal operation. In some cases, the third indication can indicate overpressure as described herein. The third indication can be different from one or more of the first or second indications.

The process can terminate in block 610. The process can be executed continuously or periodically, as illustrated by the transition from block 610 to block 600.

Pairing with Therapy Monitoring Device

As described herein, a therapy monitoring device can be paired with a negative pressure wound therapy device. For example, a negative pressure wound therapy device may be in proximity to a plurality of therapy monitoring devices, but only one of the devices can be monitoring pressure in a fluid flow path connecting the device to a wound. In some cases, the negative pressure wound therapy device can be fluidically connected to a plurality of wounds, and the device can be paired with a plurality of therapy monitoring devices. Pairing the negative pressure wound therapy device with one or more device can ensure that the negative pressure wound therapy device communicates with the relevant one or more devices.

In some cases, a therapy monitoring device may be assigned or associated with a unique identification code. For example, the identification code can be a barcode, QR code, electronic code (such as, retrievable via Radio Frequency Identification (RFID), Near Field Communication (NFC), Bluetooth, Zigbee, Wi-Fi, etc. communication), or the like. Identification codes can facilitate pairing a particular therapy monitoring device with a negative pressure wound therapy device, which in turn can be associated with a patient and or a particular wound on a patient. For example, the negative pressure wound therapy device can pair with the therapy monitoring device via scanning the barcode or QR code, exchanging data (which can include the code) using NFC, Bluetooth, RFID, Zigbee, Wi-Fi, etc., or the like. The negative pressure wound therapy device can register the unique identification code (or codes) and process only indications received from the paired devices (or devices).

Pairing can be automatic, for example, when the device and therapy monitoring device are in range of each other (sometimes referred to as "just works"). Pairing can involve exchange and verification of a code, such as a pin (sometimes referred to as "pin pairing"). In some cases, using automatic pairing can result in pairing with a wrong therapy monitoring device located in proximity of the device. Using pin pairing can be cumbersome because it may necessitate the user to enter the code.

The therapy monitoring device can transmit one or more signals through a fluid flow path, which can include one or more conduits or lumens, fluidically connecting the negative pressure wound pressure therapy device and the wound dressing. The negative pressure wound therapy device can be configured to receive the transmitted one or more signals. The signal can be acoustic (including a pressure wave), electromagnetic (including optical), or the like. Because the one or more signals are transmitted through the fluid flow path, the likelihood of receiving signals from a therapy monitoring device that is located in the proximity of the negative pressure wound therapy device but is not transmitting signal through the fluid flow path can be reduced or eliminated. Accordingly, the likelihood of the negative pressure wound therapy device pairing with an incorrect therapy monitoring device can be reduced or eliminated.

Figure 7:
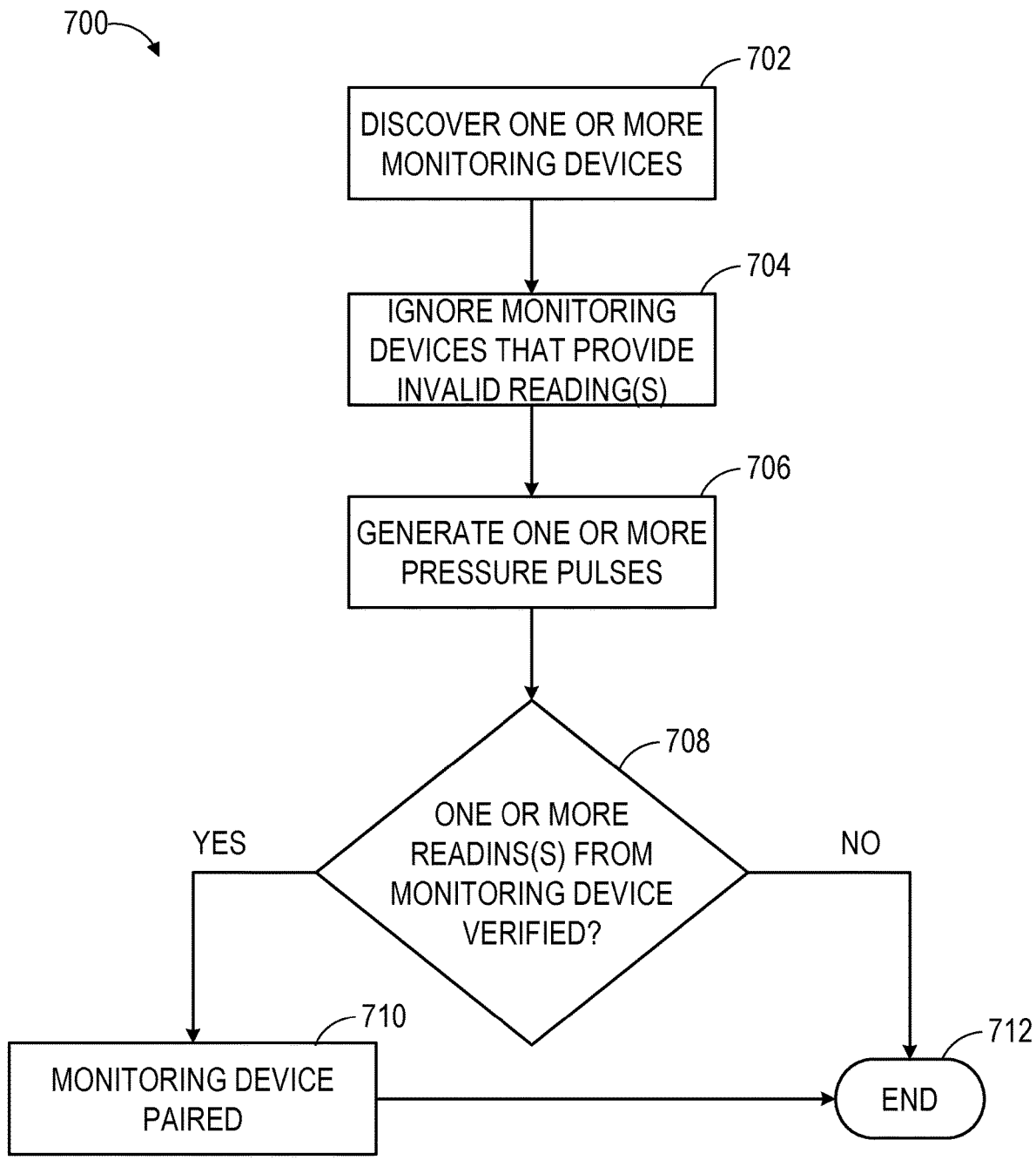
FIG. 7 illustrates a process for pairing with one or more therapy monitoring devices.

FIG. 7 illustrates a pairing process 700. The process 700 can be performed by a negative pressure wound therapy system (such as, the system 100) that includes one or more therapy monitoring devices (which can include one or more features disclosed herein). The process 700 can be implemented by at least one processor of a negative pressure wound therapy device, such as the processor 310 alone or in combination with the processor 330.

In block 702, the negative pressure wound therapy device can scan for (or discover) one or more therapy monitoring devices, which may be located in proximity of the device. A therapy monitoring device can operate in a pairing mode (sometimes referred to as advertising mode) in which the therapy monitoring device can transmit a signal. The signal can include a pressure value, which can be measured pressure or some other value (such as, predetermined value). The therapy monitoring device can transmit the signal periodically. The therapy monitoring device can transmit the signal in response to receiving an input, such as a button press by the user, responsive to detecting that negative pressure wound therapy is being applied (as described herein), or the like. In some cases, the signal can include an identifier or code associated with one or more of the therapy monitoring device or dressing. For example, the code can be associated with one or more of type, functional capabilities, etc. of one or more of the therapy monitoring device or wound dressing. The negative pressure wound therapy device can process the code to determine if one or more of the therapy monitoring device or dressing are compatible with the device. Transmission of the code can further narrow the number of therapy monitoring devices that the negative pressure wound therapy device evaluates for pairing.

The negative pressure wound therapy device can create a list of candidate therapy monitoring devices based on receiving one or more signals (which may include one or more codes). In some cases, such as illustrated in block 704, the negative pressure wound therapy device can further filter out one or more of therapy monitoring devices in response to determining whether a pressure value transmitted by a particular therapy monitoring device is valid. For example, the negative pressure wound therapy device may perform the pairing prior to activating the negative pressure source to provide negative pressure. If a particular therapy monitoring device transmits a non-zero pressure value, the negative pressure wound therapy device can determine that the particular therapy monitoring device is not a correct therapy monitoring device for pairing.

In some cases, the negative pressure wound therapy device can perform additional or alternative filtering of one or more therapy monitoring devices by causing the negative pressure source to deliver one or more negative pressure pulses to the wound, as illustrated in block 706. The negative pressure pulses may vary from 0 mmHg to −200 mmHg (or more or less). In block 708, the negative pressure wound therapy device can verify that a signal received from a therapy monitoring device includes a pressure value that matches the pressure of the negative pressure pulses at a particular time. The pulses can be provided at particular one or more frequencies. Matching can be based on one or more of intensity, duration, frequency (or pulsing speed), or the like. A match can indicate that the therapy monitoring device is measuring pressure in the fluid flow path connecting the negative pressure wound therapy device to the wound. If there is a match, the negative pressure wound therapy device can pair with the therapy monitoring device, as illustrated in block 710. Pairing can involve noting identification information of the therapy monitoring device, such as registering the unique identification code of the monitoring device with the negative pressure wound therapy device.

In case of a series of pulses, the negative pressure wound therapy device can verify that a series of signals received from the therapy monitoring device includes pressure values that match the pressures of the pulses. The series of negative pressure pulses can be varied in one or more of intensity, frequency, or the like. For example, the intensity can vary according to step, triangular, trapezoid, sinusoidal, sawtooth, or the like waveform. The negative pressure wound therapy device can be configured to verify that the signals received from the therapy monitoring device include a pressure value that matches the pressure of the negative pressure pulses over a period of time. For example, the period of time can correspond to a response time of the therapy monitoring device. The negative pressure wound therapy device can be configured to verify that the signals received from the therapy monitoring device correspond to the one or more frequencies of the series of the pressure pulses.

Once pairing has been performed, as shown in block 710, the process 700 can end in block 712. If the verification fails, the process 700 can end in block 712.

As described herein, more than one therapy monitoring device can be paired with the negative pressure wound therapy device. For example, the device can be fluidically connected to two or more wounds.

In some cases, once a therapy monitoring device has been paired, the therapy monitoring device can operate in the low power mode as described herein. The negative pressure wound therapy device can provide an indication to the therapy monitoring device that the therapy monitoring device has been paired. The indication can be provided acoustically (such as, via a pressure pulse or series of pressure pulses at a particular intensity and/or pattern), electromagnetically, or the like. The therapy monitoring device can be configured to switch to the low power mode in response to an expiration of a duration of time during which the therapy monitoring device has not been paired with a negative pressure wound therapy device.

The therapy monitoring device can be configured to be deactivated (which can include unpairing). For example, the therapy monitoring device can be configured to be deactivated in response to, after being paired, not detecting pressure in the operating range over a duration of time, such as 5 hours or less, 8 hours, 10 hours or more, or the like. Additionally or alternatively, the therapy monitoring device can be configured to be deactivated in response to, after being paired, not detecting negative pressure pulses at particular one or more frequencies, such as 0.1 (or less) to 1000 (or more) pulses/second. The therapy monitoring device can be deactivated when the power source becomes depleted.

Activation Responsive to Application of Negative Pressure Wound Therapy

The therapy monitoring device can operate in a standby mode or state (also sometimes referred to as deep sleep state), in which the least amount of power is being consumed so as to conserve the capacity of the power source. In some cases, less power is consumed in the standby mode than in any other mode described herein, such as the low power mode. For instance, the therapy monitoring device can operate in the standby mode while it is being stored, transported, or otherwise not in use (such as, not having been positioned in a fluid flow path). In the standby power mode, one or more components of the therapy monitoring device, such as the transmitter, control circuitry, or the like can be inactive. The therapy monitoring device can transition from the standby power mode to a different mode in response to detection of application of negative pressure wound therapy. For example, the therapy monitoring device can transition from the standby power mode to the low power mode. At least one of the components of the therapy monitoring device, which had been inactive in the standby mode, can be activated responsive to the transition.

As described herein, the therapy monitoring device can be configured to operate in the first power state, in which the pressure sensor periodically measures pressure in the fluid flow path, and in the second power state, in which, responsive to detecting that pressure measured by the pressure sensor is outside the operational range, the signal indicative of the detection of the operating condition is generated. The therapy monitoring device can transition from the standby power mode to the first power state, in which the therapy monitoring device can function in the low power mode.

Application of negative pressure wound therapy can cause pressure in the fluid flow path (such as, at the wound) to decrease (or become more negative). Sensing a pressure decrease that satisfies one or more pressure difference thresholds (selected or determined to be indicative of application of negative pressure wound therapy) can be used to determine that negative pressure wound therapy is being applied. As described herein, the therapy monitoring device can include a pressure sensor configured to measure pressure in the fluid flow path. The pressure sensor can be configured to provide differential or absolute pressure measurements.

For example, the pressure sensor can include a port or be otherwise exposed to the surrounding environment (such as, atmosphere) and provide differential pressure measurements relative to the surrounding environment. Because a differential pressure sensor takes into account changes in the pressure in the surrounding environment (such as, changes due to altitude, transport, etc.), a therapy monitoring device that utilizes a differential pressure sensor can detect application of negative pressure wound therapy by directly measuring a pressure decrease. The pressure decrease can be compared to a pressure difference threshold (or multiple pressure difference thresholds). In response to determining that the pressure difference threshold has been satisfied (such as, met or exceeded), a determination that negative pressure wound therapy is being applied can be made. For example, the pressure difference threshold can be selected to match the negative pressure set point, such as the lowest negative set point (for instance, about −20 mmHg or less or more, −25 mmHg or less or more, −30 mmHg or less or more, −40 mmHg or less or more, or the like).

As another example, the pressure sensor can provide absolute pressure measurements. For example, the pressure sensor can be sealed inside an enclosure or cavity (for example, sealed inside the wound dressing). Measurements by such pressure sensors may not take into account changes in the pressure in the surrounding environment. Instead of utilizing a pressure decrease as the indication of application of negative pressure wound therapy, a rate of pressure change can be used to detect application of negative pressure wound therapy, as describe herein. The rate of pressure change can be determined and compared to a threshold rate of pressure change (or multiple threshold rates of pressure change). In response to determining that the threshold rate of pressure change has been satisfied (such as, met or exceeded), a determination that negative pressure wound therapy is being applied can be made.

Atmospheric pressure can vary due to altitude variation, temperature variation, humidity variation, or the like. For example, atmospheric pressure at sea level is approximately 760 mmHg (or about 14.7 psi). Some cities in the world are at 5,000 meters above the sea level, where atmospheric pressure is approximately half that at the sea level. Operating at such altitude results in 380 mmHg pressure drop relative to operating at the sea level. As a result, utilizing only a pressure decrease as indication of application of negative pressure wound therapy may not be feasible in view of such a large pressure drop caused by the variation in atmospheric pressure.

Pressure changes can be caused by transporting one or more of the negative pressure wound therapy devices, wound dressings, or therapy monitoring devices. For example, transport by air can cause a pressure reduction as the aircraft climbs during take-off. The rate of pressure change in the aircraft can be determined as follows. In some cases, commercial aircraft used for air freight can climb at a maximum rate of about 1000 meters/minute. The freight hold of such an aircraft can be kept pressurized to a lowest aircraft cabin pressure (for example, around 11 psi) when the aircraft is at a lowest cruising altitude of about 33,000 feet (about 10,000 meters). As a result, a pressure drop of about 3.7 psi (from 14.7 psi to 11 psi) could be expected during the climb, which may last around 10 minutes (or less or more). The rate of climb of an aircraft slows as altitude is gained. This equates to a rate of pressure change of around −20 mmHg/minute (0.37 psi/minute).

Figure 8:
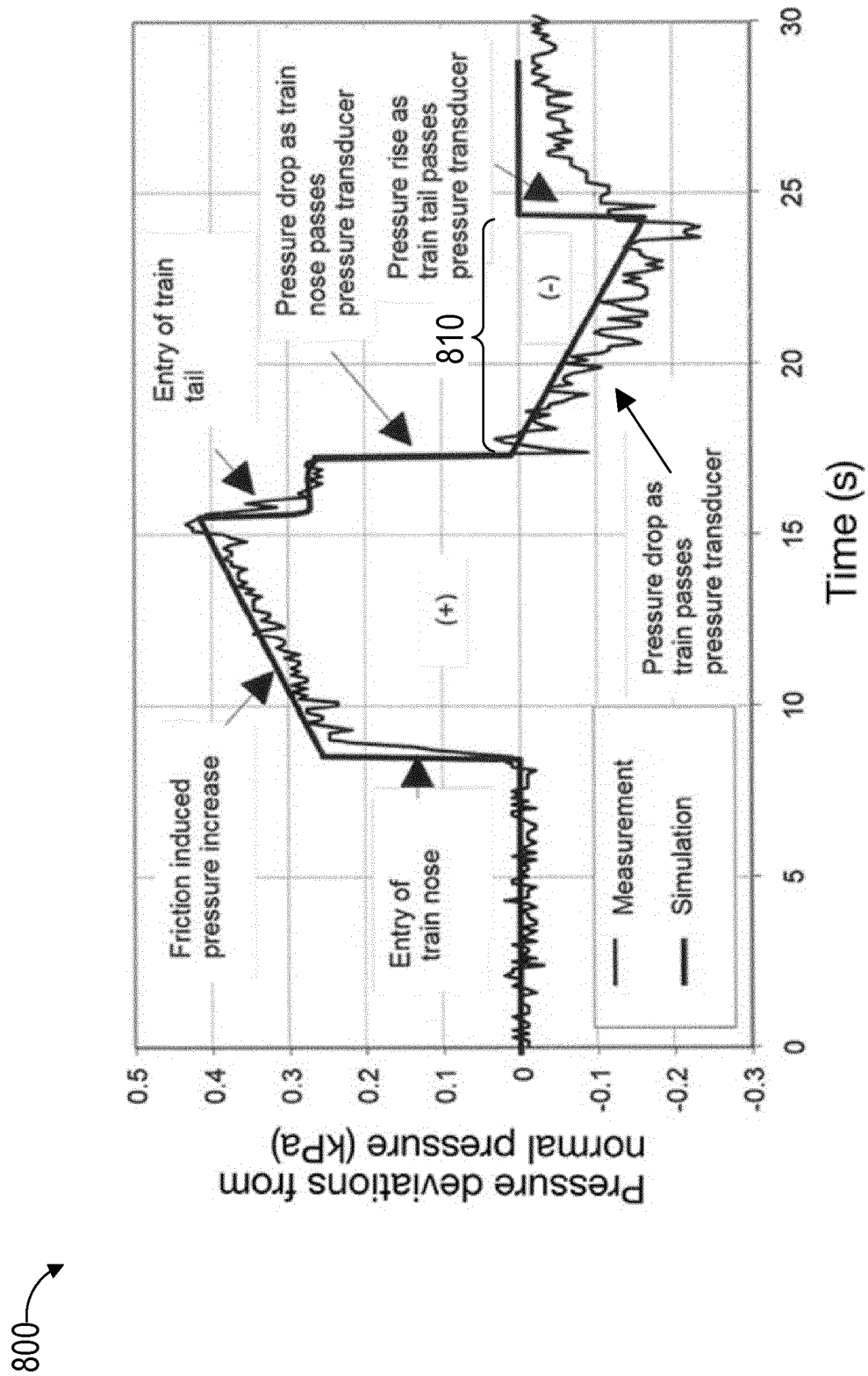
FIG. 8 illustrates pressure changes when a train travels through a tunnel.

As another example, a pressure drop can be experienced during transport by rail, such as when a high-speed train enters (or exits) a tunnel. FIG. 8 illustrates a graph 800 showing pressure changes resulting from a train travelling at around 200 km/hour entering (or exiting) a tunnel having a cross-sectional area of about 70 square meters. As is illustrated in region 810, a pressure drop can occur at a rate of about −0.2 kPa (−1.5 mmHg) over approximately 7 seconds. This equates to a rate of pressure change of about −13 mmHg/minute. While this value could be higher for different train and tunnel configurations, the rate of pressure change can be limited for passenger comfort to values similar to aircraft take-off.

In some cases, negative pressure wound therapy devices can be used to treat large wounds, whose volume can be about 4 liters (or less or more). In practice, because much of this volume may be made up by the wound dressing (such as, foam or gauze wound filler), the pressure drop caused by the initial application of negative pressure wound therapy may be more rapid at the start of therapy. This can be due to unconstrained fluid (such as, air) being first aspirated from the fluid flow path, such as from one or more lumens. Subsequently, the rate of pressure change can slow down due to constrained fluid being aspirated from the wound filler. Assuming a linear pressure drop over such initial application of negative pressure wound therapy and taking into account that the negative pressure source can aspirate more fluid at lower pressure settings (for example, at a negative pressure set point of about −40 mmHg (or less or more), it can be determined that the negative pressure source aspirates fluid at a rate of about 4 liters/minute (or less or more). The set point for a 4-liter wound volume can be established in around 1 minute, which can result in a rate of pressure change of about −40 mmHg/minute. At higher negative pressure set points (such as, −200 mmHg or less or more), the negative pressure source may aspirate fluid at a lower rate, for instance about 2 liters/minute (or less or more). The set point for a 4-liter volume wound can be established in about 2 minutes, resulting in the rate of pressure change of about −100 mmHg/minute.

At lower set points, the rate of pressure change can be smaller than at higher set points. The threshold rate of pressure change for detecting application of negative pressure can be set to match the smallest rate of pressure change. For the above example, the threshold rate of pressure change of about −40 mmHg/minute can be used. This threshold rate of pressure change is about twice as large as the rate of pressure change experienced during transport by air or rail. Thus, the risk of incorrect detection of application of negative pressure caused by pressure changes during transport can be minimized. Other threshold rates of pressure change can be utilized, such as less than −40 mmHg/minute (for instance, about −20 mmHg/minute, −30 mmHg/minute, etc.) or greater than −40 mmHg/minute (for instance, −50 mmHg/minute, −60 mmHg/minute, etc.).

In some instances, the therapy monitoring device can be configured to detect application of negative pressure wound therapy responsive to detecting that the threshold rate of pressure change (or the pressure difference threshold) is satisfied over a time duration. This approach can lessen the risk of inadvertent detection due to transient pressure changes. The time duration can be 10 seconds or less, 20 seconds or less or more, 30 seconds or less or more, 1 minute or less or more, 2 minutes or less or more, etc. The pressure sensor can be sampled at a suitable sampling rate, such as every second or less or more, every 2 seconds or less or more, every 5 seconds or less, or more, every 10 seconds or less or more, or the like. In response to detecting that the rate of pressure change satisfies the threshold rate of pressure change (or the pressure difference threshold) over the time duration, a determination that negative pressure wound therapy is being applied can be made. The below table illustrates some possible variations for such determination.

| Parameter | Minimum value (approx.) | Maximum value (approx.) |
|---|---|---|
| Threshold rate of pressure change | −20 mmHg/minute | −40 mmHg/minute |
| Sampling rate | 100 Hz | 0.016 Hz |
| Time duration | 10 seconds | 120 seconds |

In some cases, responsive to the determination that negative pressure wound therapy is being applied has been made, the therapy monitoring device can attempt to pair with a negative pressure wound therapy device using any of the approaches described herein. The therapy monitoring device can activate the transmitter so that pairing can be attempted. If pairing has not been successfully completed within a time period (such as, 1 minute or less or more, 2 minutes or less or more, 5 minutes or less or more, or the like), the therapy monitoring device can transition to the standby mode in order to conserve power. When pairing cannot be accomplished within the time period, it can be assumed that the therapy monitoring device was inadvertently activated.

In some implementations, if delivery negative pressure wound therapy has been turned off or stopped, the negative pressure wound therapy device can provide an indication to the therapy monitoring device. In response, the therapy monitoring device can transition to the standby mode in order to conserve power. In some cases, the therapy monitoring device can periodically verify that negative pressure wound therapy is being applied by utilizing any of the approached disclosed herein. In response to no longer detecting that negative pressure wound therapy is being applied, the therapy monitoring device can transition to the standby mode. This transition can be made responsive to expiration of a period of time subsequent to the detection that negative pressure is not being applied, for example, 10 minute or less or more, 30 minutes or less or more, 45 minutes or less or more, 1 hour or less or more, etc. As described herein, the therapy monitoring device can transition out of the standby mode responsive to detection of application of negative pressure wound therapy (following a restart of negative pressure wound therapy).

In some cases, the therapy monitoring device can transition out of the standby mode responsive to a user's action. For example, one or more of the therapy monitoring device or wound dressing can include a user interface for activating the therapy monitoring device, such as one or more of a switch, button, tab (such as, pull tab), or the like. In some variations, the transmitter of the therapy monitoring device can be activated (or at least periodically activated) in the standby mode. Application of negative pressure wound therapy can be communicated to the transmitter by the negative pressure wound therapy device.

Figure 9:
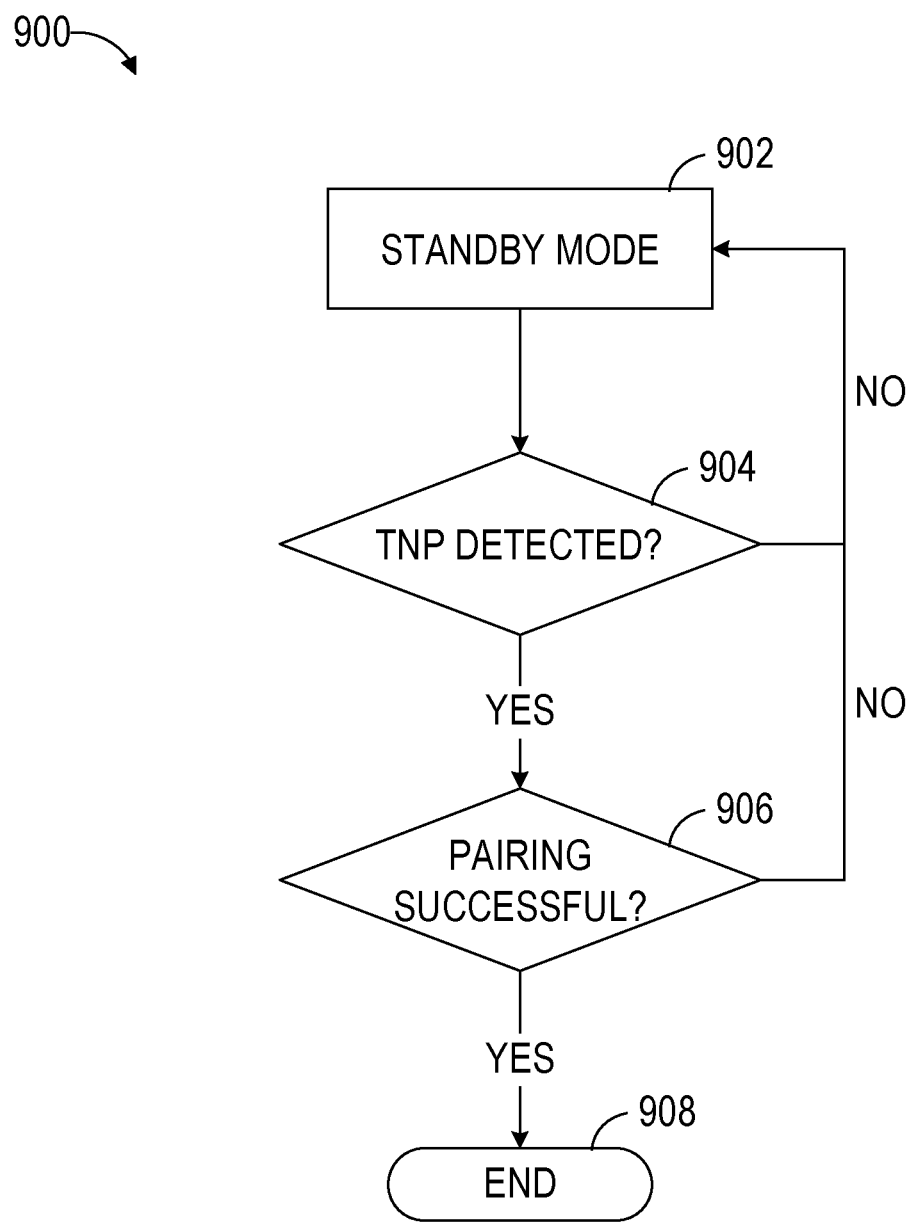
FIG. 9 illustrates a process for activating a therapy monitoring device.

FIG. 9 illustrates a process 900 for activating a therapy monitoring device. The process can be implemented by any of the therapy monitoring devices described herein. In block 902, the therapy monitoring device can operate in the standby mode. As described herein, in the standby mode the therapy monitoring device can detect in block 904 if negative pressure wound therapy is being applied. This detection can be performed periodically, such as every minute or less or more, every 2 minutes or less or more, every 5 minutes or less or more, or the like. If the detection is successful, the process 900 can transition to block 906. The therapy monitoring device can transition out of the standby mode (for example, to the low power mode, the first power state, etc.) in response to detection that negative pressure wound therapy is being applied. In block 906, the process 900 can verify whether pairing with a negative pressure wound therapy device is successful. If not, the process 900 can transition to block 902, in which the therapy monitoring device operates in the standby mode. If pairing is successful, the therapy monitoring device can operate as described herein. The process 900 can end by transitioning from block 906 to block 908.

One or more of the features of therapy monitoring devices described herein can be applicable to remote pressure sensing. For instance, a remote pressure sensing module or apparatus can be positioned in the fluid flow path. The pressure sensing apparatus can be positioned at the wound, such as be at least partially supported by the dressing, fluidic connector, or the like. The pressure sensing apparatus can include at least one pressure sensor configured to measure pressure and a transmitter configured to communicate with the negative pressure wound therapy device, such as communicate measured pressure value(s) to the negative pressure wound therapy device. As described herein, the pressure sensing apparatus can operate in the standby mode in which, for instance, the transmitter is deactivated. As described herein, the pressure sensing apparatus can transition from the standby mode to another mode (such as, the lower power mode) in which the transmitter is activated. In such another mode, the pressure sensing apparatus can monitor pressure and communicate pressure value(s) to the negative pressure wound therapy device. Systems and method for remote pressure sensing are described in U.S. patent application Ser. No. 16/919,684, filed on Jul. 2, 2020, which is incorporated by reference in its entirety.

Treatment of Multiple Wounds

Any of the negative pressure wound therapy devices disclosed herein can treat a plurality of wounds. A plurality of therapy monitoring devices can be positioned in the fluid flow path according to any of the approaches described herein. In some cases, the therapy monitoring devices can be used to separately detect the operating condition for at least some wounds (or for each wound) of the plurality of wounds. Systems and method for treating multiple wounds are described in U.S. patent application Ser. No. 16/919,684, filed on Jul. 2, 2020, which is incorporated by reference in its entirety.

OTHER VARIATIONS

Although some embodiments describe negative pressure wound therapy, the systems, devices, and/or methods disclosed herein can be applied to other types of therapies usable standalone or in addition to TNP therapy. Systems, devices, and/or methods disclosed herein can be extended to any medical device, and in particular any wound treatment device. For example, systems, devices, and/or methods disclosed herein can be used with devices that provide one or more of ultrasound therapy, oxygen therapy, neurostimulation, microwave therapy, active agents, antibiotics, antimicrobials, or the like. Such devices can in addition provide TNP therapy. The systems and methods disclosed herein are not limited to medical devices and can be utilized by any electronic device.

Any of transmission of data described herein can be performed securely. For example, one or more of encryption, https protocol, secure VPN connection, error checking, confirmation of delivery, or the like can be utilized.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Conditional language used herein, such as, among others, "can," "could", "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language, such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A negative pressure wound therapy monitoring device comprising:
    a housing configured to be positioned in a fluid flow path
        connecting a wound covered by a wound dressing to a source of negative pressure of a negative pressure wound therapy device or at the wound;
a user interface; and
an electronic circuitry at least partially enclosed by the housing, the electronic circuitry comprising a sensor configured to monitor at least one parameter associated with delivery of negative pressure wound therapy by the source of negative pressure, the electronic circuitry configured to:
responsive to manipulation of the user interface by a user, transition from an off state in which the electronic circuitry is not operating to operating in a first state in which the sensor periodically measures a value of the at least one parameter;
in response to detecting with the sensor that the value of the at least one parameter is outside an operational range, transition from operating in the first state to operating in a second state and generate an indication of abnormal delivery of the negative pressure wound therapy, the indication configured to be detected by the negative pressure wound therapy device; and
in response to receiving an indication from the negative pressure wound therapy device that provision of negative pressure wound therapy has been stopped, transition from operating in the second state to operating in the first state.

2. The device of claim 1, wherein the indication of abnormal delivery of the negative pressure wound therapy comprises indication of at least one of a leak in the fluid flow path, an overpressure in the fluid flow path, or non-compliance with a duration of negative pressure wound therapy.

3. The device of claim 1, further comprising a power source configured to power the electronic circuitry, wherein less power is consumed by the electronic circuitry in the first state than in the second state.

4. The device of claim 3, wherein the first state comprises a low power state during in which capacity of the power source is conserved, and wherein the electronic circuitry is further configured to transition to operating in the low power state after generating the indication.

5. The device of claim 3, wherein the power source comprises an electroactive polymer configured to generate power in response to one or more of application of negative pressure or loss of negative pressure.

6. The device of claim 1, wherein the indication comprises at least one of an acoustic signal or an electromagnetic signal.

7. The device of claim 1, wherein the sensor comprises at least one of a pressure sensor configured to monitor negative pressure at the wound, an oxygen sensor configured to monitor oxygen concentration at the wound, or a moisture sensor configured to monitor moisture level at the wound.

8. The device of claim 1, wherein the housing comprises an enclosure formed from substantially elastic material and enclosing a volume of gas, wherein pressure within the enclosure increases as a result of the delivery of negative pressure wound therapy, and wherein the sensor comprises a pressure sensor configured to monitor the increase in pressure in the enclosure.

9. The device of claim 1, wherein the housing is configured to be positioned on or within the wound dressing or in a fluidic connector connecting the wound dressing to the source of negative pressure.

10. The device of claim 1, wherein the operational range is associated with at least one of a minimum negative pressure level, a range of negative pressure, or a minimum duration of the negative pressure wound therapy over a period of time.

11. The device of claim 1, wherein the electronic circuitry further comprises a transmitter configured to transmit information, and wherein:
the transmitter is deactivated in the first state; and
the transmitter is activated in the second state.

12. The device of claim 11, wherein the electronic circuitry is further configured to:
subsequent to the transition from operating in the first state to operating in the second state, attempt to pair via the transmitter with the negative pressure wound therapy device; and
in response to being unable to pair, transition to operating in the first state.

13. The device of claim 12, wherein the electronic circuitry is configured to transition to operating in the first state subsequent to expiration of a duration of time over which the electronic circuitry attempts to pair.

14. The device of claim 11, wherein the sensor comprises a pressure sensor, and wherein the electronic circuitry is configured to detect provision of negative pressure wound therapy in response to a detection that pressure measured by the pressure sensor satisfies a pressure decrease threshold.

15. The device of claim 14, wherein the pressure decrease threshold comprises a pressure difference threshold indicative of a differential pressure in the fluid flow path associated with provision of negative pressure wound therapy or a rate of pressure change threshold indicative of a rate of pressure decrease in the fluid flow path associated with provision of negative pressure wound therapy.

16. The device of claim 15, wherein the pressure decrease threshold comprises the rate of pressure change threshold, and wherein the electronic circuitry is configured to detect provision of negative pressure wound therapy in response to a detection that rate of pressure change determined from pressure measurements by the pressure sensor over a period of time satisfies the rate of pressure change threshold.

17. The device of claim 15, wherein the rate of pressure change threshold is selected to distinguish provision of negative pressure wound therapy from a pressure decrease caused by transporting the device by aircraft or train.

18. A negative pressure wound therapy system comprising:
a negative pressure wound therapy device comprising a controller and a negative pressure source configured to be fluidically connected via a fluid flow path to a wound dressing positioned over a wound, the negative pressure source further configured to provide negative pressure therapy to the wound via the fluid flow path; and
a therapy monitoring device configured to be positioned in the fluid flow path or at the wound, the therapy monitoring device further configured to 1) transmit one or more first signals via the fluid flow path and 2) monitor a parameter associated with the provision of negative pressure wound therapy and generate a second signal in response to detecting that a value of the parameter is outside an operational range,
wherein the controller is configured to:
pair with the therapy monitoring device in response to detecting the one or more first signals transmitted via the fluid flow path and verifying that one or more pressure characteristics indicated by the one or more first signals matches one or more expected pressure characteristics;

detect the one or more first signals generated by the therapy monitoring device;

verify that the therapy monitoring device is paired with the negative pressure wound therapy device; and in response to the verification:
- determine if the negative pressure source has been activated to provide negative pressure to the wound; and
- in response to the determination that the negative pressure source has been activated, generate an alarm associated with the one or more first signals.

19. The system of claim 18, wherein the controller is configured to:

cause the negative pressure source to deliver a set of negative pressure pulses via the fluid flow path;

receive the one or more first signals indicating a pressure measured by the therapy monitoring device; and pair with the therapy monitoring device in response to determining that the one or more first signals indicate the pressure that matches a pressure of the set of negative pressure pulses.

20. The system of claim 19, wherein the controller is configured to:

cause the negative pressure source to deliver a plurality of negative pressure pulses via the fluid flow path;

receive the one or more first signals indicating a frequency measured by the therapy monitoring device; and pair with the therapy monitoring device in response to determining that the one or more first signals indicate the frequency that matches a frequency of the plurality of negative pressure pulses.

* * * * *